(12) United States Patent
Imran

(10) Patent No.: US 9,974,797 B2
(45) Date of Patent: May 22, 2018

(54) SOLID DRUG DELIVERY APPARATUS, FORMULATIONS AND METHODS OF USE

(71) Applicant: InCube Labs, LLC, San Jose, CA (US)

(72) Inventor: Mir Imran, Los Altos Hills, CA (US)

(73) Assignee: InCube Labs, LLC, San Jose, CA (US)

( * ) Notice: Subject to any disclaimer, the term of this patent is extended or adjusted under 35 U.S.C. 154(b) by 176 days.

(21) Appl. No.: 14/732,647

(22) Filed: Jun. 5, 2015

(65) Prior Publication Data
US 2015/0265634 A1 Sep. 24, 2015

Related U.S. Application Data

(62) Division of application No. 13/645,344, filed on Oct. 4, 2012, now Pat. No. 9,072,877.
(Continued)

(51) Int. Cl.
*A61K 31/635* (2006.01)
*A61M 1/12* (2006.01)
(Continued)

(52) U.S. Cl.
CPC ....... *A61K 31/635* (2013.01); *A61M 37/0069* (2013.01); *A61M 5/14276* (2013.01); *A61M 2205/04* (2013.01)

(58) Field of Classification Search
CPC ........ A61M 31/002; A61M 2202/0464; A61M 37/0069; A61M 2205/04; A61M 1/12; A61M 5/14276
See application file for complete search history.

(56) References Cited

U.S. PATENT DOCUMENTS 4,531,938 A * 7/1985 Kaye ................. A61M 37/0069
 206/528
4,548,607 A 10/1985 Harris
(Continued)

FOREIGN PATENT DOCUMENTS

CN 1829547 A 9/2006
JP 2006528500 A 12/2006
(Continued)

OTHER PUBLICATIONS

International search report dated Dec. 26, 2012 for International Application No. PCT/US2012/058813.
(Continued)

*Primary Examiner* — Quynh-Nhu H Vu
(74) *Attorney, Agent, or Firm* — Wilson Sonsini Goodrich & Rosati; Joel M. Harris, Esq.

(57) ABSTRACT

Embodiments provide apparatus and methods for delivering solid form medications such as pellets to various locations in the body. One embodiment provides an apparatus for in vivo delivery of medication pellets comprising a housing including a port, a pellet-containing belt disposed in the housing, and a mechanism for transferring the pellets from the belt to a delivery site (DS) outside the housing. Each pellet contains a dose of drug to treat a medical condition. An elongate member is coupled to the housing and includes a lumen for pellet delivery, a proximal end coupled to the port and a distal end positioned at the DS. The pellet can be delivered to the DS at regular intervals or responsive to a detected biological event. Embodiments of the invention are particularly useful for delivering medication to treat a medical condition over an extended period without requiring a patient to take external medication.

20 Claims, 26 Drawing Sheets

Related U.S. Application Data

(60) Provisional application No. 61/626,909, filed on Oct. 4, 2011.

(51) Int. Cl.
*A61M 37/00* (2006.01)
*A61M 5/142* (2006.01)

(56) References Cited

U.S. PATENT DOCUMENTS

| | | | | |
|---|---|---|---|---|
| 4,759,371 A | * | 7/1988 | Franetzki | A61B 5/14528 600/373 |
| 4,976,686 A | * | 12/1990 | Ball | A61M 37/0069 604/61 |
| 5,997,500 A | * | 12/1999 | Cook | A61M 37/0069 604/141 |
| 9,072,877 B2 | | 7/2015 | Imran | |
| 2006/0196504 A1 | * | 9/2006 | Augustyn | A61M 15/0045 128/203.15 |
| 2007/0255237 A1 | | 11/2007 | Lobl et al. | |
| 2010/0330149 A1 | | 12/2010 | Daniel et al. | |
| 2012/0296259 A1 | * | 11/2012 | Imran | A61M 31/002 604/20 |

FOREIGN PATENT DOCUMENTS

| | | |
|---|---|---|
| JP | 2009535155 A | 10/2009 |
| WO | WO 9607440 A2 | 3/1996 |
| WO | WO-0054660 A1 | 9/2000 |
| WO | WO 2005/014089 A1 | 2/2005 |
| WO | WO-2010051369 A1 | 5/2010 |
| WO | WO 2010107507 A1 | 9/2010 |

OTHER PUBLICATIONS

Notice of allowance dated Mar. 5, 2015 for U.S. Appl. No. 13/645,344.
Office action dated Aug. 15, 2014 for U.S. Appl. No. 13/645,344.
European search report written opinion dated Nov. 18, 2015 for EP Application No. 12837798.3.

\* cited by examiner

Pre Energy/Force Delivery

Post Energy/Force Delivery

SOLID DRUG DELIVERY APPARATUS, FORMULATIONS AND METHODS OF USE

CROSS-REFERENCE TO RELATED APPLICATIONS

This application is a divisional of U.S. patent application Ser. No. 13/645,344, filed Oct. 4, 2012, which claims benefit of priority to U.S. Provisional Patent Application No. 61/626,909, filed Oct. 4, 2011, the aforementioned priority applications being incorporated herein by reference in their entirety.

This application is also related to U.S. patent application Ser. No. 12/661,774, filed Mar. 22, 2010, entitled "Solid Drug Delivery Apparatus and Formulation"; and Ser. No. 12/661,767, filed Mar. 22, 2010, entitled "Methods of Solid Drug Delivery" which are both incorporated by reference herein in their entirety for all purposes.

BACKGROUND OF THE INVENTION

Field of the Invention

Embodiments of the invention relate to drug delivery devices and methods of use thereof. More specifically, embodiments of the invention relate to implantable drug delivery devices for the delivery of solid form drugs and other therapeutic agents.

The current trend in many medical treatments requires the delivery of a drug to a specific target site so as to avoid the toxicity to other tissue, as well as more precisely controlling the timing and amount of drug delivered to that site. In many cases, this can require an implantable drug pump. However, due to their size and power requirements the current available pumps do not lend themselves to many medical applications, particularly for delivery of medication to the brain, heart and other tissues, where very precisely controlled doses of drug can be required. Also current devices can require frequent replenishment of the drug due to limited reservoir size and/or limited shelf life of the drug. Thus, there is a need for improved implantable drug delivery devices and associated methods for in vivo drug delivery.

BRIEF SUMMARY OF THE INVENTION

Embodiments of the invention provide apparatus, systems, formulations and methods for delivering medications in solid form to various locations in the body of a human patient or mammal many embodiments provide an implantable apparatus for delivering medication in solid form wherein the medication includes one or more solid form drugs for treating various medical conditions such as epilepsy and other neural condition; diabetes and other endocrine conditions; and cardiac arrhythmias and other cardiac rhythm disorders. Particular embodiments provide an enclosed implanted apparatus for delivering solid form medications such as pellets to a delivery site so as to treat a medical condition for an extended period of time. Embodiments also provide various solid form medications or formulations comprising one or more drugs to be delivered by embodiments of the apparatus or other drug delivery apparatus.

One embodiment provides an apparatus for in vivo delivery of solid form medications or formulations comprising a housing containing: i) one or more belts including a plurality of doses of medication; and ii) a delivery mechanism for engaging the belt and transferring an individual dose of medication from the belt through a port in the housing wall to a selected tissue delivery site. In many embodiments, the mechanism comprises an advancement member such as a metal wire and an advancement means such as pinch rollers for advancing the advancement member, for example, by pushing the advancement member. The doses of medication will typically be individually packaged in packaging containers (e.g., also referred to as packaging) that are integral or otherwise attached to the belt. The packaging containers are typically sealed and in preferred embodiments, are hermetically sealed. In one embodiment, the packaging container can correspond to sealed foil packaging. According to one or more embodiments, the advancement member is be configured to push the solid form medication out of the sealed packaging container and through the port in the housing.

According to one or more embodiments the solid form medication is formulated into pellets, though other solid formulations are also contemplated (e.g., powder, nanoparticles, etc). Each pellet contains a selected dose of a drug to treat a particular medical condition(s) such as epilepsy, arrhythmia or diabetes. The dose can be selected based on the patient's weight, age and particular condition including severity of the condition (e.g., moderate vs. severe arrhythmia). Also, the medication pellets are desirably formulated using one or more pharmaceutical excipients, including for example, disintegrants so as disintegrate and dissolve the pellets in a controlled fashion to achieve and maintain a sufficient concentration of the drug (either at the tissue site, plasma or other tissue location) for treatment of the condition. The pellets are also desirably fabricated so as to have a product life of years or longer in vivo so the drug maintains its potency and therapeutic effectiveness. The pellets can include a plurality of drugs for treatment of a condition or conditions, for example, a cocktail of antiviral drugs for treatment of HIV AIDS.

According to one or more embodiments, the belt can configured to hold and dispense a plurality of doses of medication. The belt can be spring loaded or use other advancement means. Desirably, the belt contains a sufficient supply of medication pellets to provide treatment of the condition for an extended period of time, for example, two years or longer.

In many embodiments, an elongate member such as a catheter can be coupled to an opening in the housing. The elongate member has a lumen sized to receive the medication pellet, a proximal end coupled to the port or other housing opening and a distal end or tip that extends through an opening in the housing to deliver the pellet to a target tissue site. Desirably, the distal tip has an atraumatic configuration to allow for extended periods of implantation at the target tissue site without a foreign body response such as inflammation, etc. The same advancement wire (or other advancement member) which is used to push the pellet out of the packaging container is also used to push or advance the pellet into the elongate member lumen and out to the target tissue site.

In many embodiments, the apparatus is coupled to a controller for controlling one or more aspects of the medication delivery process including, for example, actuation and control of the drive source to deliver a medication pellet. The controller can also be programmed to include a delivery regimen wherein medication is delivered at a selected regular intervals (e.g., once or twice a day, etc.) over an extended period. It can also be configured to receive a signal (e.g., wireless or otherwise) to initiate the delivery of medication or to change the delivery regimen (e.g., from once a day to twice a day). In this way, the patient or a medical care provider can titrate the delivery of medication in response to a specific event (e.g., an episode of angina or an epileptic pre-seizure event) or to longer term changes in the patient's condition or diagnosis or both.

According to one or more embodiments, the controller can be operably coupled to or otherwise receive inputs from an implanted sensor, such as a glucose sensor, which senses a physiologic/biological parameter indicative of a condition to be treated by the medication in the pellet, for example, diabetic hyperglycemia (treated by insulin) or an epileptic seizure (treated by furosemide). When the controller receives an input from the sensor indicative of the condition, it initiates the delivery of one or more medication pellets to the target tissue site so as to treat the medical condition. Both the initial and subsequent inputs from the sensor can be used to titrate the delivery of medication pellets over an extended period until the condition is dissipated or otherwise treated. The controller can also receive inputs from other sensors configured to measure the plasma/blood or other tissue concentration of the delivered drug. These inputs can also be used to titrate the delivery of the medication to achieve a selected concentration of drug (e.g., in plasma, tissue, etc.) as well as a selected pharmacokinetic profile. The drug sensors can be positioned at the target tissue site as well as other sites in the body (e.g., a vein or artery) in order to develop a pharmacokinetic model of the distribution of the drug at multiple sites in the body. The apparatus can also include a sensor coupled to the controller which indicates when the supply of medication pellets has been exhausted up and/or exactly how many medication pellets are left. The controller in turn, can signal this information to an external communication device such as a cell phone, portable monitor or remote monitor (e.g., at the physician's office). In this way, the patient and/or medical care provider can take appropriate action well before the apparatus runs out of medication.

The pellets or other solid form of the medication are delivered to a delivery site such as subcutaneous tissue where they are configured to be broken, disintegrate and absorbed by body tissue fluids so as to produce a desired concentration of the drug at a target tissue site. In some applications, the delivery site can be the same as the target site, for example the brain. In other applications, the target site can be different from the delivery site, for example, the delivery site can be intramuscular tissue in the chest and the target site can be the heart or the liver. The delivery site can be adjacent the target site, for example adipose to deliver to underlying muscle tissue, or it can be placed at a non-oppositional site, for example, intramuscular delivery to reach the site of the heart. In each case, the medication pellet can include a selected dose of drug and be configured to disintegrate and be dissolved by body tissue fluids so as to yield a therapeutically effective concentration of the drug at the target tissue site. In many applications, this involves the pellet being dissolved by body tissue fluids at the delivery site (e.g., interstitial fluids) where the drug then diffuses from the tissue into the blood stream where it is carried to the target tissue site. Accordingly, in these and other applications, the dose of the drug in the pellet can be titrated to achieve a selected plasma (or other tissue compartment) concentration of the drug (or concentration range) for a selected period during and after dissolution of the pellet.

In some embodiments, the pellet (including the drug dose) is configured to disintegrate and be dissolved by the tissue fluids within a body compartment such as the cerebrospinal fluid (CSF) in the brain so as to achieve a selected concentration in the tissue fluid within that compartment. In particular embodiments for treating various neural disorders such as epileptic and other seizures, the pellet is configured to rapidly disintegrate and be dissolved in the CSF so as to rapidly achieve a selected concentration of the drug throughout the CSF bathing the brain to prevent the occurrence of the seizure or lessen its duration and severity. This can be achieved through the use of one or more super disintegrants as well as disintegrating enhancing features (e.g., pores, cracks or other intrusions) in or on the pellet. It can also be achieved by treating the pellet prior to or after delivery with mechanical, electromagnetic, acoustical or other energy to weaken the pellet structure, create cracks and other structural defects for the ingress of fluids or initiate the breakup of the pellet into smaller pieces. In other embodiments, a solid form medication for delivery within the body of a patient is provided, the medication comprising at least one drug for the treatment of a disease or condition, wherein the medication has a shape and material properties so as to be: (i) be stored in a container implanted within the body for an extended period without substantial degradation or deleterious effect to the medication, (ii) delivered to a delivery site, and (iii) dissolve in tissue fluids at the delivery site to produce a therapeutic effect at a target tissue site to treat the disease or condition.

In various applications, embodiments of the invention can be used to deliver solid form drugs to provide treatment for a number of medical conditions including epileptic seizures, high blood pressure, elevated cholesterol, diabetes, coronary arrhythmia's (both atrial and ventricular), coronary ischemia (e.g., from a heart attack and/or stenosed coronary artery), cerebral ischemia, stroke, anemia or other like condition. The apparatus can be implanted at or near the target tissue site (e.g., the brain) or at remote delivery site (e.g., subdermally, intramuscularly in the chest or thigh). Further embodiments of the invention can be used to provide concurrent treatment for two or more of these or other conditions eliminating the need for the patient to take multiple doses of multiple drugs (e.g., orally or by parenteral means) over the course of day. This is particularly beneficial to patients who have long term chronic conditions including those who have impaired cognitive abilities.

In an exemplary embodiment of a method for using the invention, the apparatus can be implanted at a selected delivery site (e.g., the brain, or the pectoral region for delivery to the heart) depending on the condition to be treated. Implantation can be done using an open or minimally invasive surgical procedure known in the art. Prior to implantation, the apparatus can be loaded with one or more belts described herein having a selected number of pellets (or other solid drug formulation) to provide for delivery of pellets to the delivery site over an extended period of time, e.g., months or years. Once implanted, the pellets can be stored in the apparatus for an extended period of time (e.g., 1, 2, 5 years or longer) without degradation or deleterious effect to the pellets (e.g., loss of drug potency or therapeutic effectiveness) due to the fact that the pellets are stored in sealed packaging. The apparatus can deliver solid form medication to the delivery site at regular intervals (e.g., once a day, week, month, etc.) or in response to an input from a sensor. In the latter case, the input can be indicative of a particular medical condition or biological/physiological event such as an epileptic seizure or pre-seizure event. A controller described herein can be used to determine when to initiate delivery based on the sensor input and/or the time intervals for delivery for embodiments employing delivery at regular intervals. In either case, the controller can send a signal to the mechanism to deliver a drug pellet from the housing interior to the tissue site. There the drug pellet disintegrates/degrades and is dissolved in local tissue fluids to treat a local target tissue site (e.g., it dissolves in the CSF to treat the brain), or it is subsequently absorbed into the blood stream where it is carried to a remote target tissue site (e.g., the liver, heart, etc.) or both. Further, pellets can be delivered based on input from a sensor providing physiologic data predictive of the medical condition (e.g., blood glucose) or another sensor that is configured to sense the local and/or plasma concentration of the drug. In some embodiments, pellet delivery can be controlled by sensing the state of disintegration of previously delivered pellets. For example, another pellet can be delivered when it has been determined that the previous pellet is in a particular state of disintegration (e.g., it has been completely or substantially disintegrated). This can be achieved by sending and receiving a signal from the pellet such as an optical, ultrasound or electrical signal. For example, for the use of optical signal reflectance measurements can be used to determine the state of disintegration. A particular disintegration state can be determined when the reflectance signal falls below a particular threshold. Similar approaches can be used for use of reflected ultrasound or impedance. The pellet can even include various echogenic, or optically opaque or other agents to enhance the reflected ultrasonic, optical or other signal. The pellet may also include various optical indicia having one or more of a pattern, size or shape configured to provide an indication of the state of disintegration of the pellet.

Further details of these and other embodiments and aspects of the invention are described more fully below, with reference to the attached drawing figures.

BRIEF DESCRIPTION OF THE DRAWINGS

FIG. 2A shows the septum in the closed state; and FIG. 2B shows the septum in the open state to allow passage of a medication pellet.

FIG. 9A shows placement of the entire apparatus in the brain for delivery of medication to a target site in brain tissue; FIG. 9B shows placement of the apparatus on the scalp with a delivery catheter extending into brain tissue; FIG. 9C shows an embodiment of the apparatus having two delivery catheters positioned at two different delivery sites; FIG. 9D shows an embodiment of the apparatus having two delivery catheters with the first delivery catheter positioned near or in the knee joint and the second delivery catheter positioned at a different location.

FIG. 12A shows the pellet before the delivery of force or energy; and FIG. 12B shows the pellet after the delivery of force or energy to create cracks.

DETAILED DESCRIPTION OF THE INVENTION

Embodiments of the invention provide apparatus, systems, formulations and methods for delivering medications in solid form to various locations in the body. Many embodiments provide an implanted apparatus for delivering medication in solid form wherein the medication includes one or more solid form drugs or other therapeutic agents for treating various medical conditions such as epilepsy, diabetes, high blood pressure, and high cholesterol. Particular embodiments provide an enclosed implanted apparatus for delivering solid form medications to a delivery site DS and ultimately to a target tissue site TS (herein target site TS), such as the brain or heart, to treat a medical condition for an extended period of time. Embodiments also provide various solid form medications or formulations comprising one or more drugs to be delivered by embodiments of the apparatus or other solid drug delivery apparatus.

Figure 1:
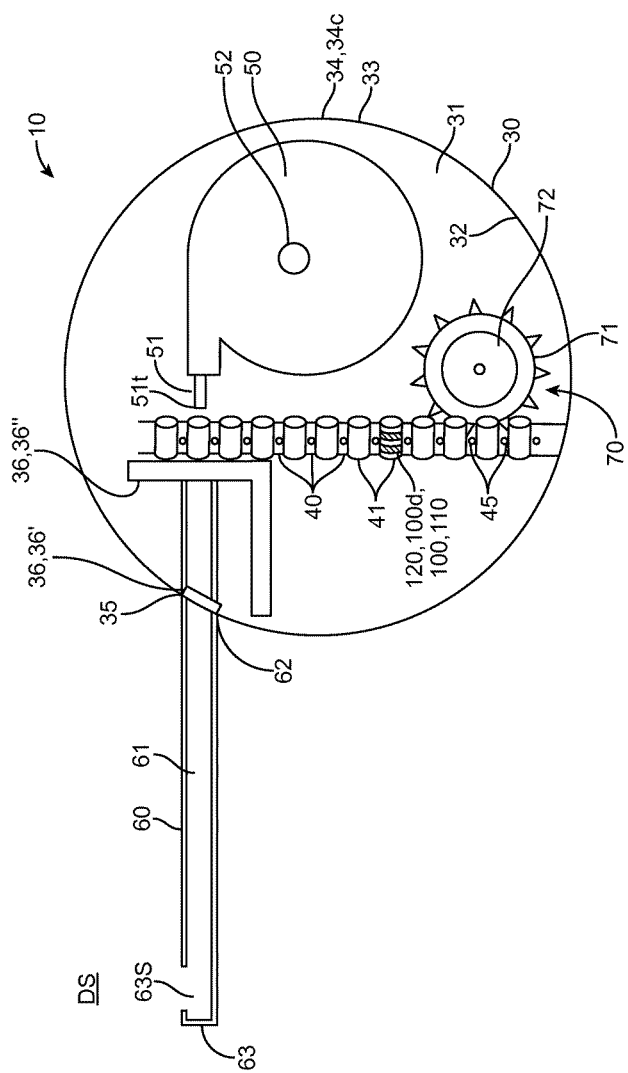
FIG. 1 illustrates an embodiment of a solid drug delivery apparatus.
Figure 1A:
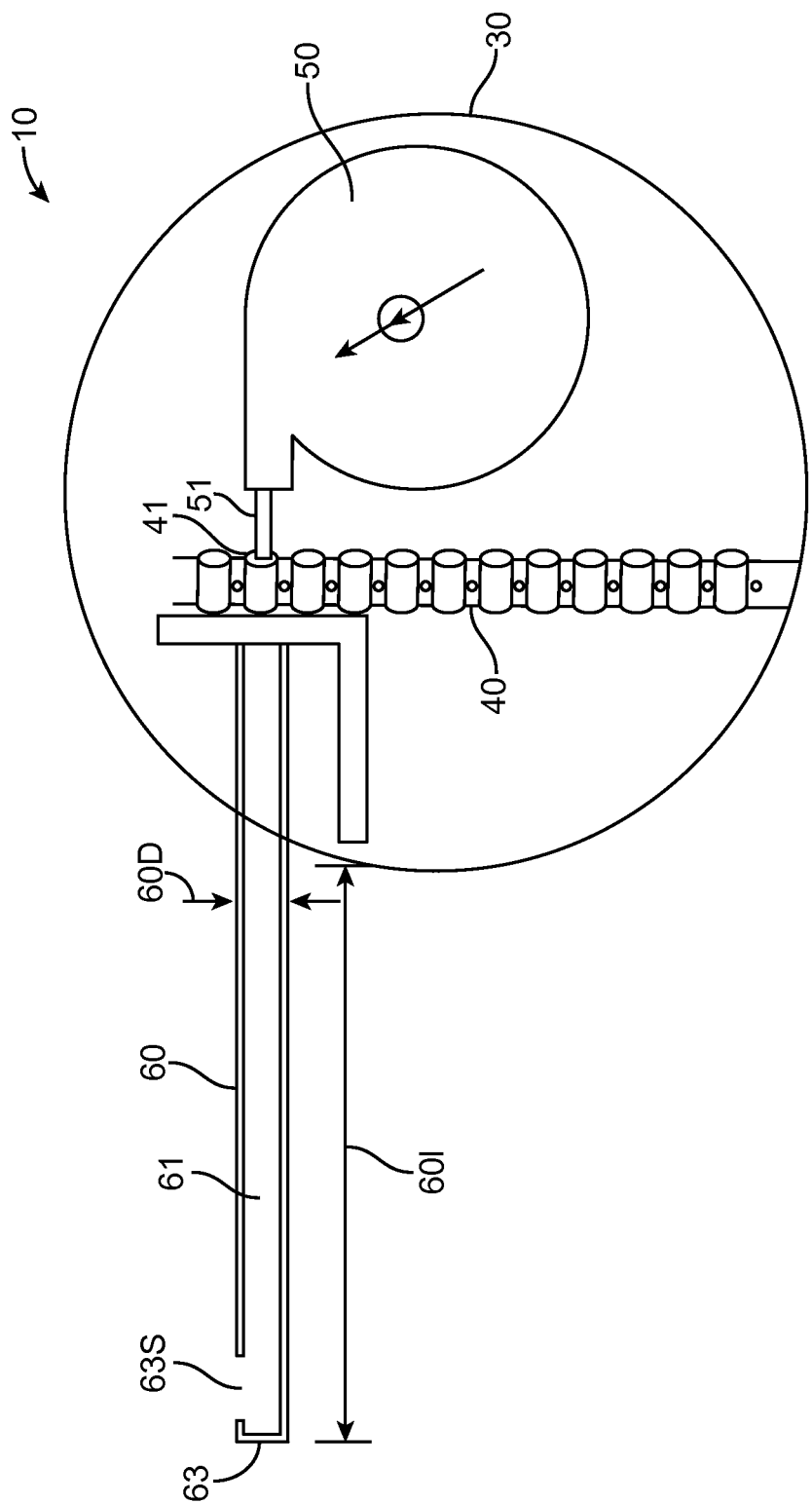
FIGS. 1A-1F illustrate use of the apparatus of the embodiment of FIG. 1 to deliver a medication pellet or other form of medication to a delivery site in the body of a patient.
Figure 1B:
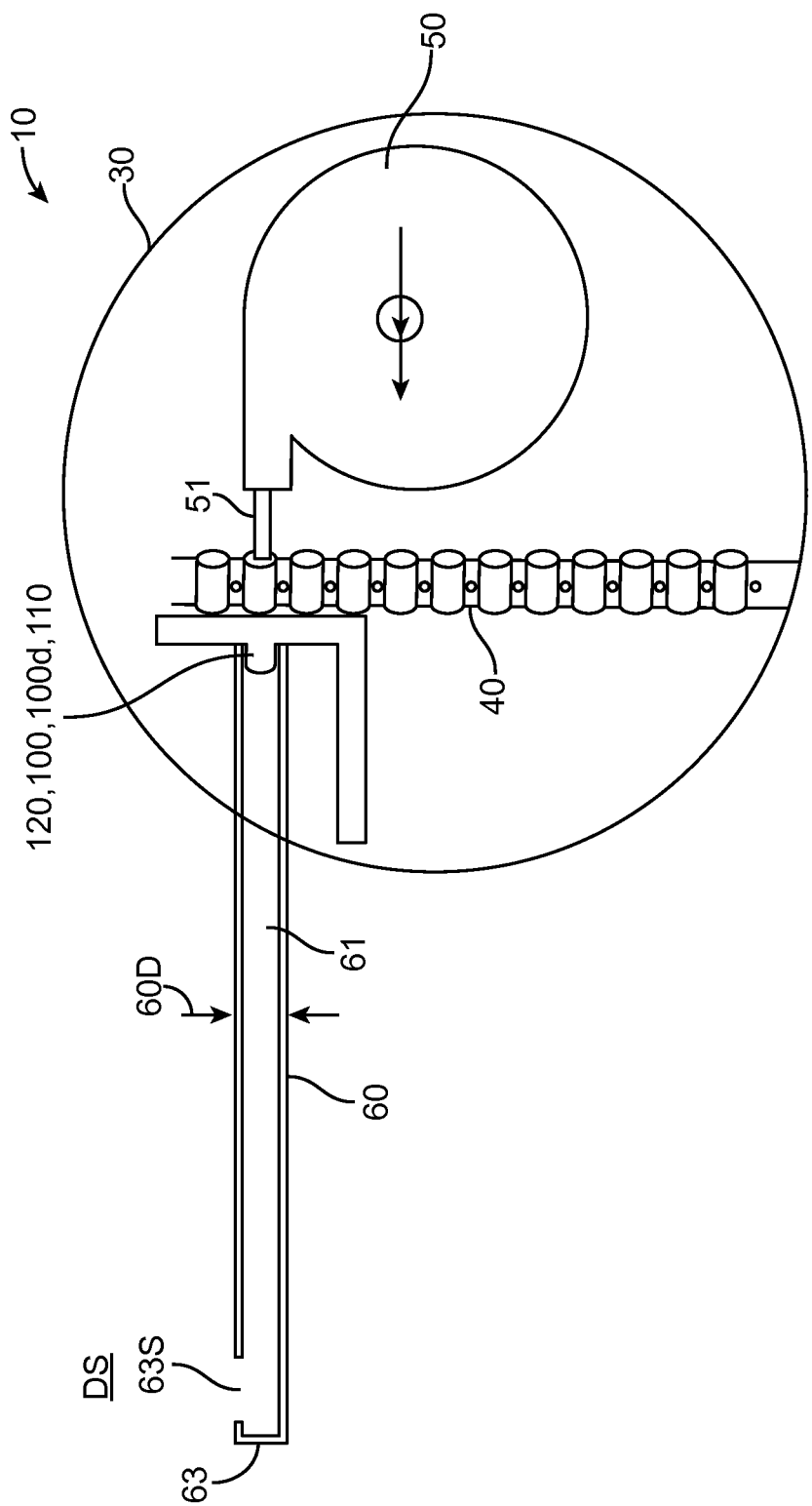
Figure 1C:
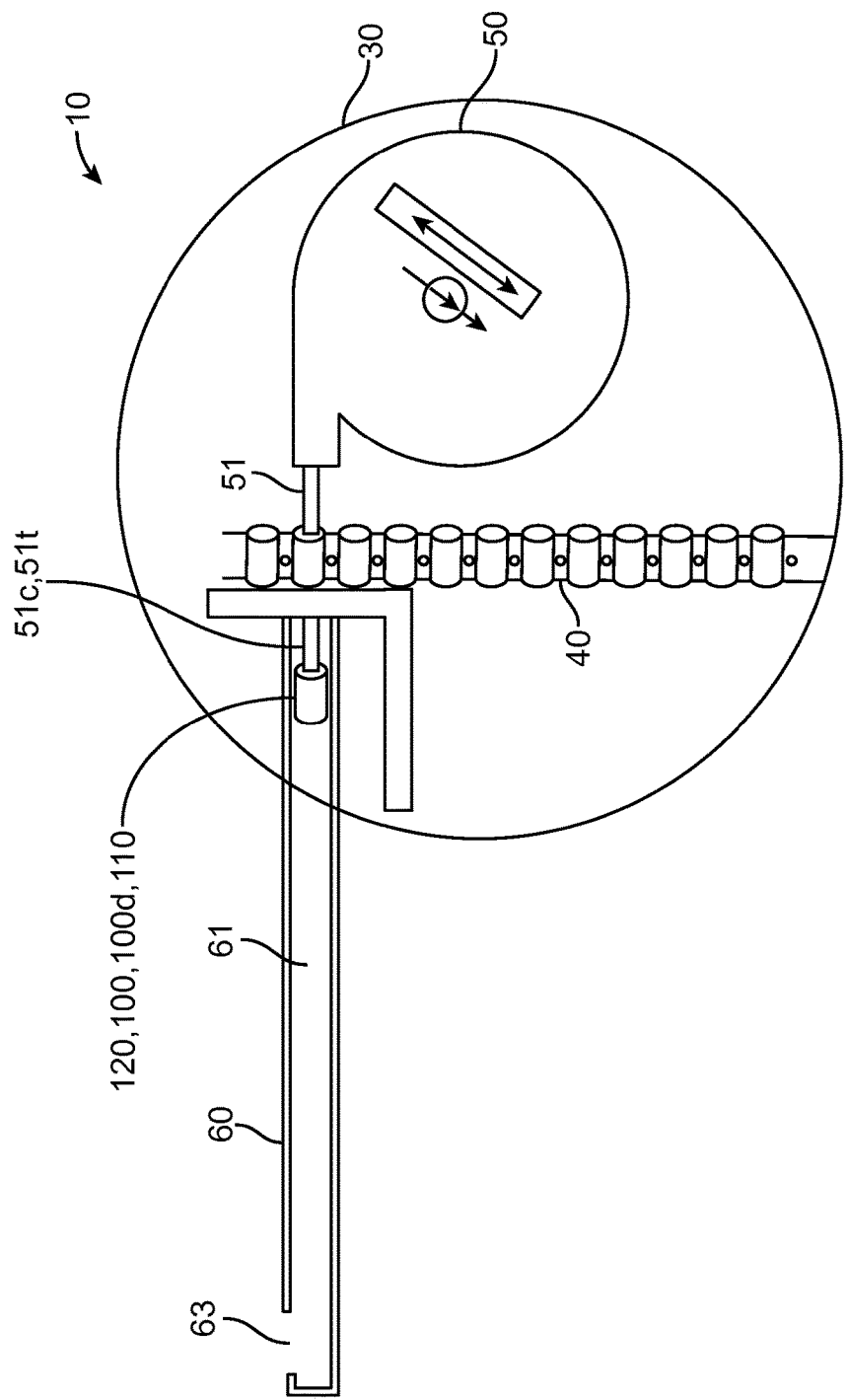
Figure 1D:
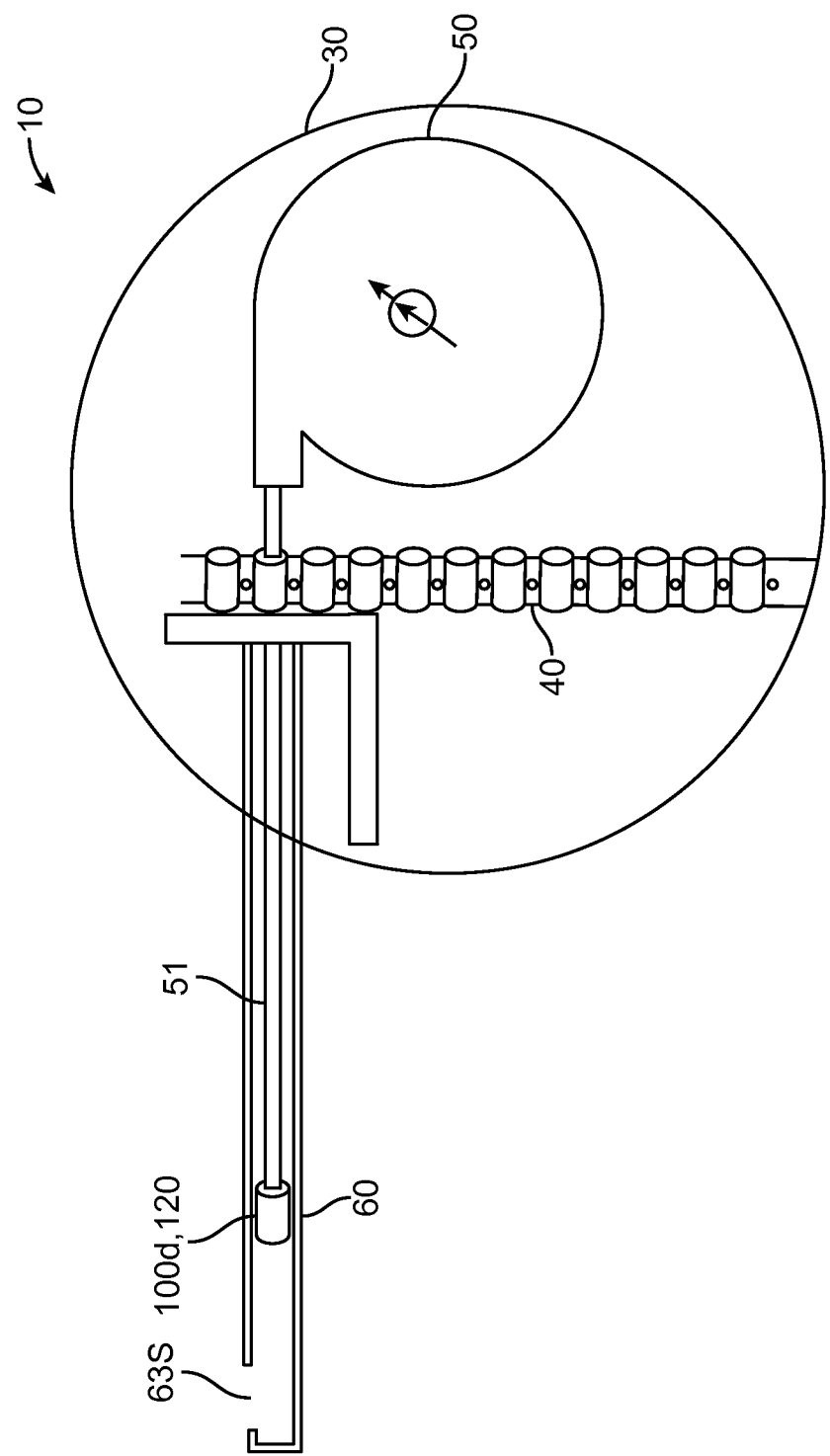
Figure 1E:
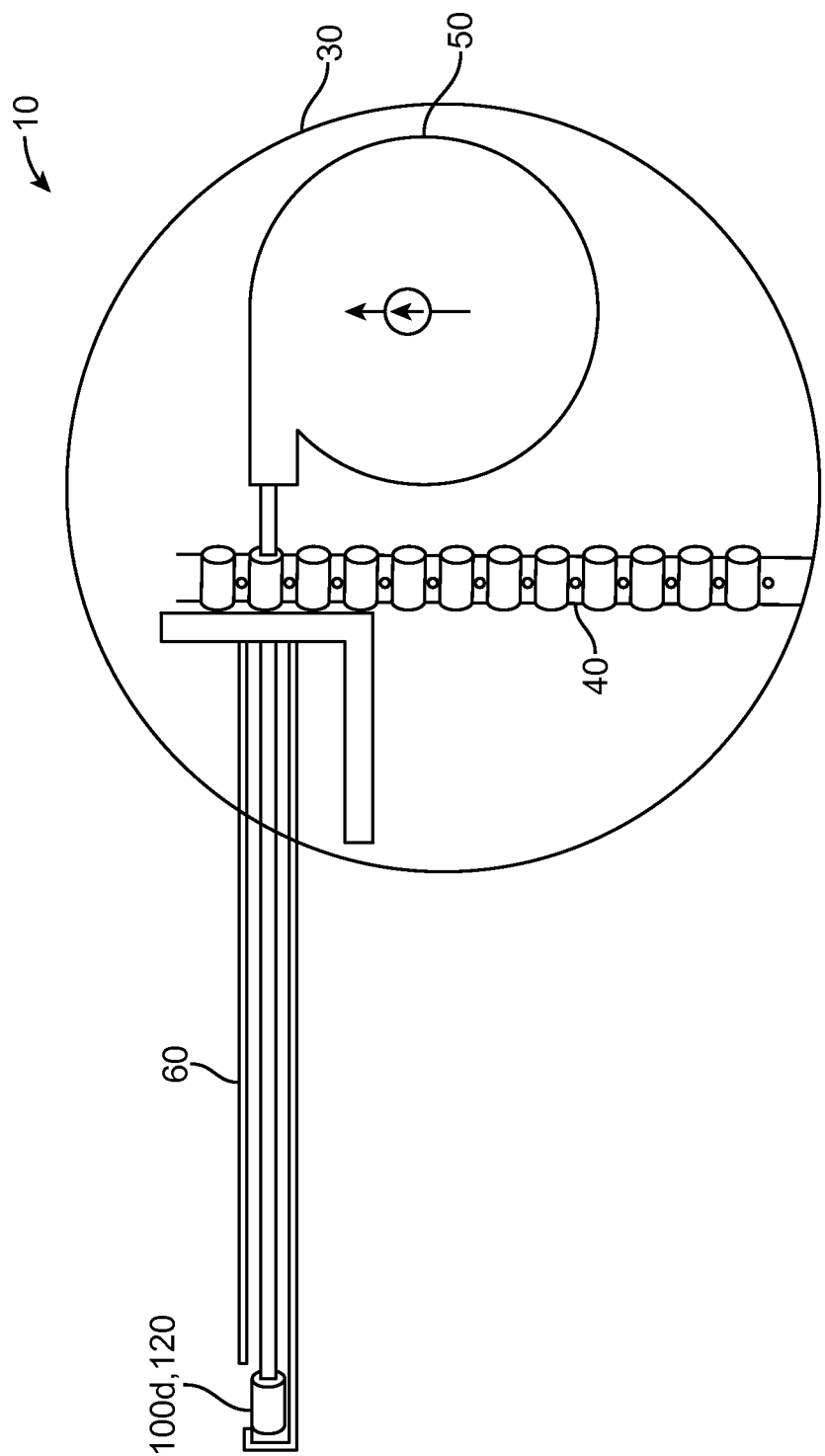
Figure 1F:
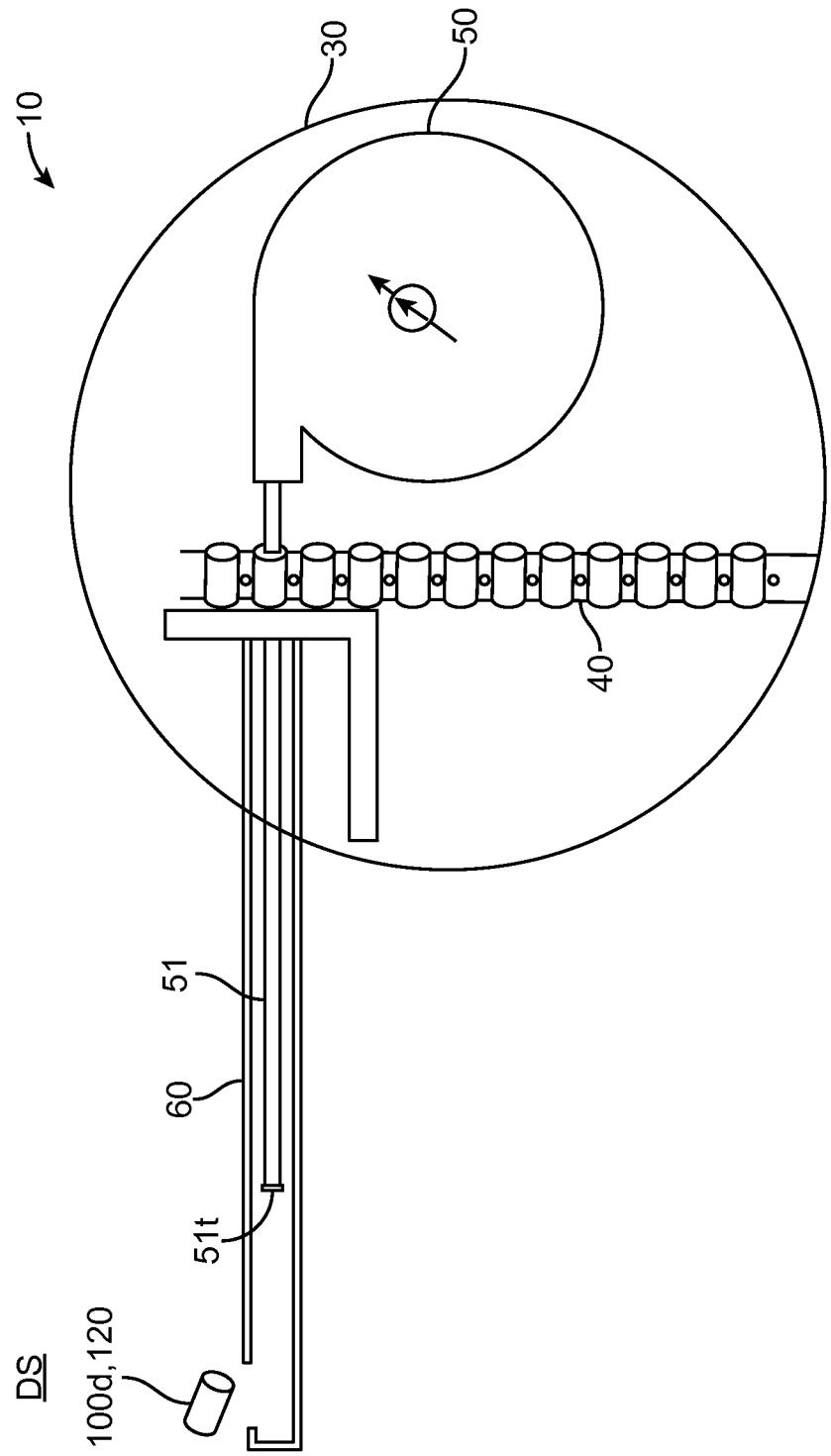

Referring now to FIGS. 1 and 1A-1F, an embodiment of an apparatus 10 for the delivery of a solid form medication 100 to a delivery site DS, includes a housing 30 having an interior 31, an interior surface 32 and exterior surface 33 and a port 35. As will be discussed herein, in many embodiments, port 35 is coupled to an elongate member 60 (also referred to herein sometimes as an elongated member 60) such as a catheter 60 having a lumen 61, a proximal end 62 coupled to opening 35 a distal end 63 positioned at a tissue delivery site DS for delivery of solid medication 100 as is shown in the embodiment of FIG. 1. Solid form medication 100 also described herein as formulation 100, medication 100 will typically be formulated into pellets 100, though other solid formulations are also contemplated as is described herein. Medication 100 includes one or more drugs or other therapeutic agents 110 to treat one more medical conditions such as various endocrine, cardiovascular or neural conditions.

Housing 30 (also referred to herein as container 30 or chamber 30) contains a drug belt 40 having a plurality of doses 100*d* of medication 100 and a delivery mechanism 50 (also referred to herein as transfer mechanism 50) for engaging belt 40 and transferring an individual dose 100*d* of medication 100 from the belt through port 35 to deliver it to a selected tissue delivery site DS and a belt drive mechanism or other belt advancement means 70 for advancing the belt. Doses 100*d* are typically individual packaged in packaging 41 (also referred to herein as packaging containers 41) which is integral with or otherwise attached to belt 40. In some embodiments, multiple doses 100*d* (e.g., 2, 3, 4 or even more doses) of medical 100 may be packaged in an individual packaging container 41. As will be discussed herein, in many embodiments, mechanism 50 includes an advancement member 51, such as a wire, which is used push dose 100*d* out of packaging 41 through port 35, down elongate member 60 and to selected tissue site DS.

Figure 2A:
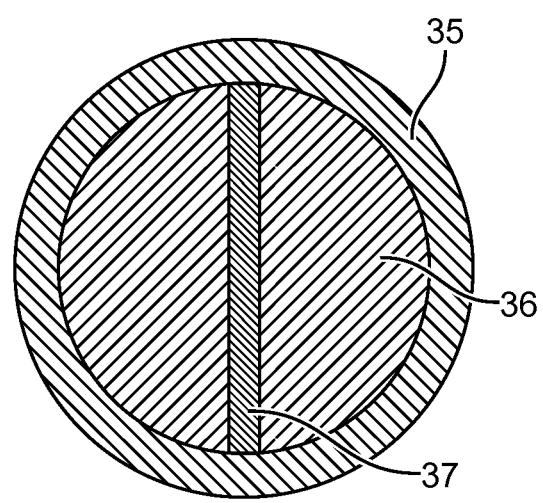
FIGS. 2A and 2B are cross sectional views illustrating an embodiment of a re-sealable septum having a slit for use with one or more embodiments of the solid drug delivery apparatus.
Figure 2B:
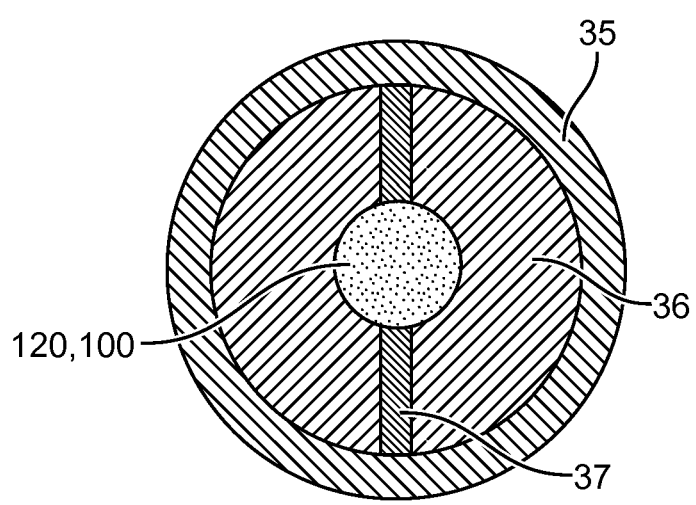

In many embodiments, port 35 comprises a sealable septum 36 allowing a solid dose of medication 100 to be passed through the septum by mechanism 50 without the ingress of fluids into housing interior 31 as is shown in the embodiments of FIGS. 2A and 2B. Septum 36 can comprise various elastomeric polymers such as silicone or polyurethane which have sufficient resilience to open and then seal itself after being punctured or otherwise opened by the passage of medication 100 such as a medication pellet 100. In particular embodiments septum 36 can have a re-sealable slit 37, that is normally in a closed state (as is shown in FIG. 2A) and is opened by the passage of medication 100 (as is shown in the embodiment of FIG. 2B) only to close again on itself after medication 100 passes through due to the elasticity and resilience of the material making up septum 36. In some embodiments apparatus 10 can include a first and second septum 36' and 36" to reduce the likelihood of fluid ingress into housing interior 31 during delivery of medication 100 as is shown in FIG. 1.

Housing 30 can correspond in size to containers used for various pacemakers, with larger and smaller sizes contemplated depending upon for example, the size and configuration of components within the housing (e.g., mechanisms 50, 70 described herein and the desired supply of medication 100). It may be fabricated from various biocompatible metals and plastics known in the art, for example, PET, fluoropolymer, PEBAX, polyurethane, titanium, stainless steel and the like. Also, the interior surface 32 or exterior surface 33 of the housing may coated with gas/water vapor impermeable materials or include gas impermeable layers 34 so as to minimize the transmission of water vapor into housing interior 31. Suitable gas/water impermeable materials include isobutyl rubbers. Housing 30 can also include one or more biocompatible coatings 31C known in the art including polyurethanes, silicones, fluoropolymers, DACRON and the like. Coating 31C can also include various eluting drugs such as various steroids known in the cardiovascular implant arts for reducing the amount of cellular and other bio-adhesion to the housing. Housing 30 can be sized and shaped to fit in various locations in the body including: the skull and cranial cavity, the chest, within in one or more GI organs, the heart, the vascular system, as well as various subcutaneous and intramuscular locations including the extremities and the trunk. All or portions of housing 30 can also be constructed from conformable materials (e.g., polyurethane silicone and other elastomeric polymers) to conform to the shape of surrounding tissue layers and compartment, e.g., the curvature on the inside of the skull, or the contour of the skin. Conforming materials can also be employed to allow for surrounding body tissue to grow around and reshape the housing during prolonged periods of implantation. In this way, embodiments having a flexible housing minimize the effect of the housing on the growth and function of surrounding tissue, thus allowing the apparatus to be implanted over very prolonged periods including allowing the apparatus to be implanted in children and remain through adulthood. Various conformable materials can also be used to facilitate implantation of apparatus 10 using minimally invasive methods. Such materials allow the apparatus including housing 30 to bend, twist or otherwise conform so as to be inserted through surgical ports and guiding devices and then reassume its shape once positioned at the intended implantation site. In particular embodiments, bending and twisting of housing 30 can be further facilitated by the use of flexible joints built in for the housing. Housing 30 can also be sized and shaped to further facilitate implantation using minimally invasive surgical methods. For example, the housing can have a particular size and shape such as a cylindrical shape to enable it pass through various minimally invasive surgical ports and guiding devices. The housing may also be configured to have a collapsed non-deployed state and an expanded deployed state where the non-deployed state is used for advancing the housing and the deployed state once the housing is positioned at a desired location in the body.

Figure 3A:
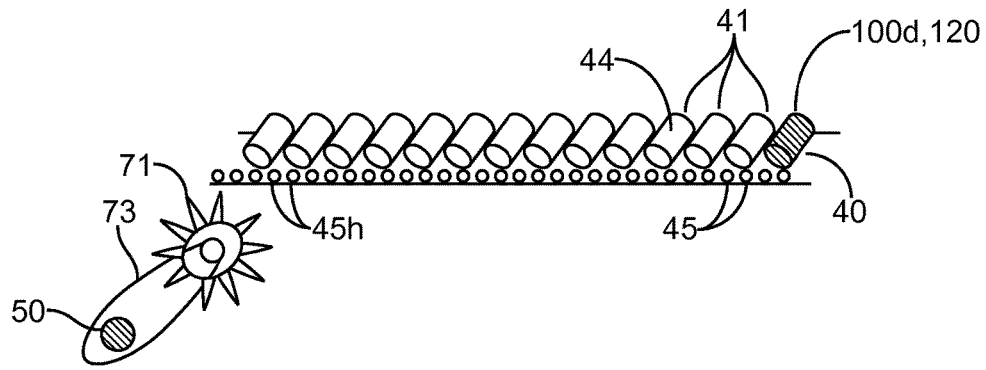
FIG. 3A is a perspective view showing an embodiment of a belt including a registration means and a plurality of medication doses contained in packaging containers that are attached to the belt on an outer surface of the packaging container.
Figure 3B:
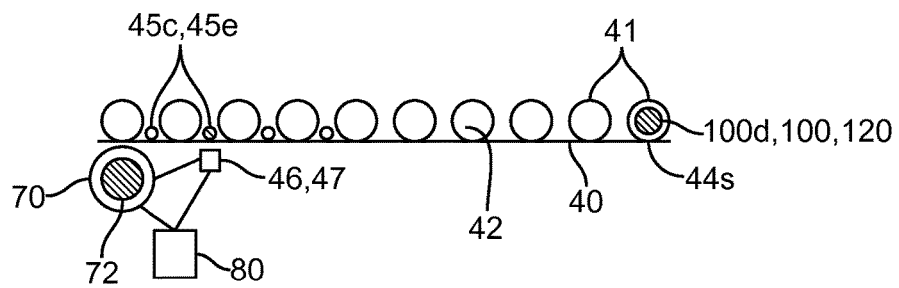
FIG. 3B is a side showing of the embodiment of FIG. 3A.
Figure 4A:
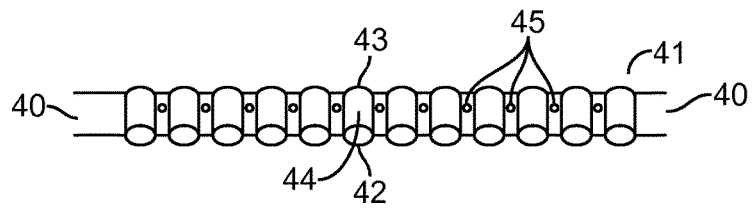
FIG. 4A is a perspective view showing an embodiment of a belt including a plurality of medication doses contained in packaging containers that are attached to the belt at a central portion of packaging container.
Figure 4B:
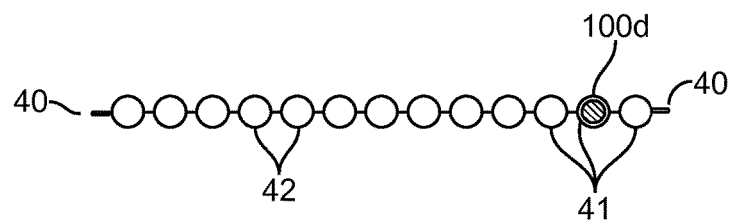
FIG. 4B is a side showing of the embodiment of FIG. 4A.

Referring now to FIGS. 3A-3B and 4A-4B, in various embodiments, belt 40 contains a plurality of doses 100*d* of solid form medication 100 and also registration means 45. In many embodiments, registration means 45 corresponds to holes 45*h* which are used to advance belt 40 by a sprocket-based belt advancement means 70 (described herein) as is shown in the embodiment of FIG. 3A. In additional or alternative embodiments, registration means 45 may correspond to: i) optically encoded indicia 45*o* allowing belt 40 to be advanced by a belt advancement means 70 coupled to an optical sensor 46 (e.g., a photodiode or CCD) for reading optical indicia 45*o*, or ii) electromagnetic indicia 45*e* allowing belt 40 to be advanced by a belt advancement means 70 coupled to an electrical sensor 47 (e.g., a conductive contact) for reading electromagnetic indicia 45*e* as is shown in the embodiment of FIG. 3B. Still other registration means are contemplated.

Belt 40 can be fabricated from various metals or polymer films known in the art such as PET and NYLON. In preferred embodiments, belt 40 comprises a stainless steel belt which can be fabricated along with registration means 45, using various chemical etching methods known in the art. According to one or more embodiments individual doses 100d of medication 100 (e.g., pellets 100) can be packaged in hermetically sealed packaging 41 (also referred to herein as packaging containers 41) each packaging container having a body 44 which can be attached to the belt or otherwise integral to it. In one embodiment shown in FIG. 3A, packaging containers 41 can be attached to belt 40 along a surface 44s of the packaging container body 44. In another embodiment shown in FIG. 4A, packaging containers 41 can be centrally attached or otherwise integral to belt 41. Such embodiments can be achieved by fabricating belt 40 and packaging containers 41 from the same metal/foil strip or other piece of material (e.g., polymer.).

Figure 5:
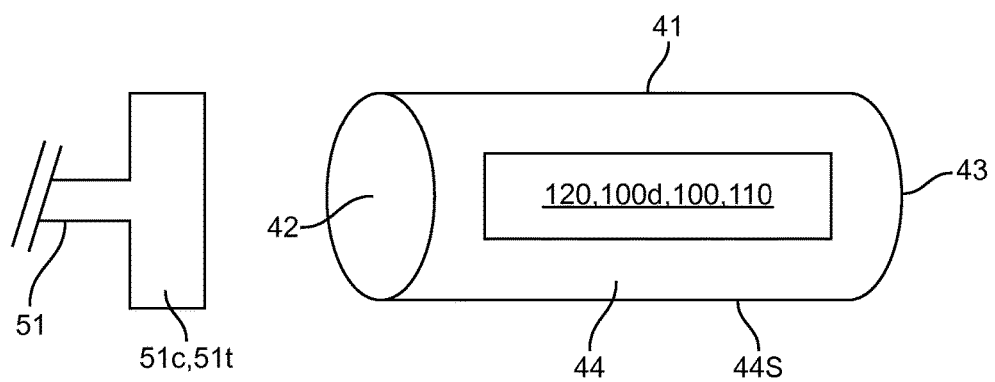
FIG. 5 is a perspective viewing showing an embodiment of an individual packaging container for a dose of solid form medication.

Typically, packaging container 41 will have a cylindrical shape having a body 44 and first and second ends 42 and 43 as shown in the embodiment of FIG. 5. However, other shapes are also contemplated. Ends 42 and 43 are desirably, configured to be puncturable by the advancement of advancement member 51, so as to allow the advancement member to push into and puncture first end 42 and then push pellet 100 through second end 43. One or both of ends 42 or 43 can be sealable to body 44 and in preferred embodiments are hermetically sealed. The ends 42 and 43 may also be fabricated from conductive material such that when they are punctured by advancement member 51, member 51 makes electrical contact completing a circuit and sending a signal back to controller 80 to thus provide an indication that both ends have been punctured. In various embodiments, packaging containers 41 can comprise various sealable foils and polymers known in the pharmaceutical packaging arts, for example, PET, HDPE, NYLON and other materials known in the art. In some embodiments, packaging container 41 may have a two-ply or other multi-ply construction for improved impermeability and shelf life. Packaging containers 41 can be attached to belt 40 using any number of attachment methods known in the art including for example, adhesive bonding, welding, ultrasonic welding, heat staking or other related method.

Desirably, belt 40 contains a sufficient supply of medication pellets 100 to provide treatment of a particular medical condition for an extended period of time, for example, one to two years, two to five years or longer. Shorter periods are also contemplated. In various embodiments, belt 40 can hold up to several hundred or more pellets 100. In various embodiments, apparatus 10 can include multiple belts 40, including two, three or more belts. In these and related embodiments, apparatus 10 can include means for switching over from a first to a second or other belt 40. Such switching means (not shown but readily comprehendible to those skilled in the electro-mechanical arts) can include for example, a solenoid and can be stand alone or incorporated into mechanism 50 and/or belt drive mechanism 70 (described herein) for embodiments having the latter.

Figure 6:
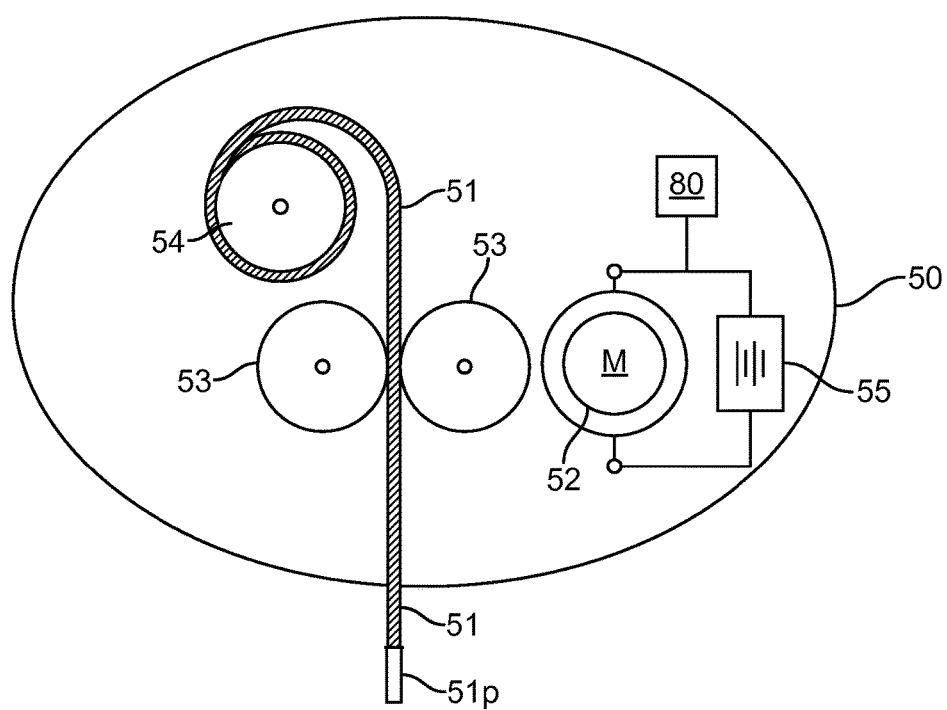
FIG. 6 is a top viewing showing an embodiment of a delivery mechanism including a drive source, advancement member, rollers and advancement member spool.

A discussion will now be presented of delivery mechanism 50 (also referred to sometimes as advancement mechanism 50), herein mechanism 50. In many embodiments, mechanism 50 comprises an advancement member 51 coupled to a drive source 52 which may be disposed in a housing (not shown). In particular embodiments, drive source 52 can be used to drive one or both of a set of pinching rollers 53 or other advancement means as is shown in FIG. 6. Pinch rollers 53 pinch down on advancement member 51 to push it out of housing 30 and then withdraw it back into the housing. Accordingly, in these and related embodiments, drive source 52 is configured to move in a linear manner in a forward and then a reverse direction as is shown in the embodiments of FIG. 1A-1F. As is discussed below, one or more of the speed, acceleration and direction of the drive source may be controlled for example, by a controller such as a controller 80 described herein. Also, in particular embodiments, advancement member 51 is kept in a wound state on a spool 54 (or other spool means 54) in a retracted position and then unwound when advanced by drive source 52 and rewound when withdrawn back into housing 30.

In various embodiments, advancement member 51 corresponds to a flexible metal wire configured to have good pushability (e.g., column strength) and trackability characteristics (as is known in the guide wire arts) when advanced by pinch rollers 53 (or other advancement means known in the art) through catheter 60 so as to be able to push medication pellet 100 out of packaging container 44, through septum or other opening 35, down the length of catheter lumen 61 and out of catheter tip 63 either directly or out of a slot 63s. Advancement member 51 is also desirably sufficiently flexible to be wound back up onto spool 54 when the advancement member is withdrawn back into housing 30. In these and related embodiments, advancement member 51 may correspond to a flexible stainless steel wire (e.g., 304 v wire) or a super elastic wire such as a NITINOL wire. For various metal wire embodiments, advancement member 51 may include an inner core for pushability and an outer coil or for enhanced flexibility and trackability. Alternatively, in some embodiments a wire based advancement member 51 may comprise a coiled wire alone having a selectable diameter and pitch to achieve the desired mechanical properties. Also, all or portions of a wire-based advancement member 51 may be coated and/or tapered to achieve desired frictional and mechanical characteristics. Coatings can include various lubricious coatings known in the art (e.g., TEFLON). Tapering can include both a smooth taper as well steeper tapers to achieve desired transition in the mechanical properties of the advancement member. In other embodiments, advancement member 51 may correspond to various resilient polymers known in the catheter arts. In one variation, all, or a portion, of advancement member 51 can itself comprise medication 100 with distal portions of the advancement member advanced through port 35 out of housing 30 for delivery to delivery site DS. The advancement member may include fixed length portions 51p corresponding to a dose 100d of medication 100 as is shown in FIG. 6. Fixed length portions 51p of a medication containing advancement member 51 may be cut or otherwise broken off from the body of the advancement member 51 using any number of cutting means known in the art which built into housing 30 and/or mechanism 50. Separation of fixed length portions 51p of a medication containing advancement member 51 may also be facilitated by use of perforations, cracks or other structural defects which are placed into the length of advancement member 51 during or after fabrication. Medication containing embodiments of advancement member 51 can be fabricating using various molding and other shape forming and compounding methods known in the pharmaceutical manufacturing arts.

As shown in FIG. 6, the length and diameter (including taper for tapered embodiments) of advancement member 51 are desirably configured such that it can track and move freely within catheter lumen 61 so as to advance medication pellet 100 out of the catheter 60 (through either tip 63 or slot 63s described below) to a selected delivery site DS. Additionally, the diameter and shape of the tip 51t (shown in FIG.

5) of the advancement member 51 are configured relative to the size of pellet 100 such that it can easily push a pellet or other form of medication 100. In some embodiments, advancement member tip 51*t* can include a cap 51C which is shaped and sized relative to the shape and size of medication pellet 100 to improve the ability of advancement member 51 to push the pellet 100 through catheter 60 as is show in FIG. 5. In some embodiments, cap 51C may have a shape which mates or otherwise complements the shape of pellet or other form of solid medication 100.

In various embodiments, drive source 52 can correspond to a mechanical drive source such as a spring; an electromechanical drive source such as an electric motor, a solenoid or a piezoelectric motor. In preferred embodiments, drive source 52 corresponds to a brushless dc motor or a stepper motor which may be controlled by a controller 80 described herein (or other controller) and is configured to move in a forward and reverse direction. Controller 80 may be used to control the speed, acceleration and direction of drive source so as to control the speed, acceleration and direction of advancement member 51 and in turn that of medication pellet 100 or other medication 100. In some embodiments, the speed of advancement member 51 can be adjusted depending upon the selected delivery site DS. For example, for delicate tissue sites such as the brain, the speed of the advancement member may be slowed down so as to reduce any potential trauma from medication pellet 100 exiting catheter 60 (the speed may even be reduced just prior to when the pellet exists the catheter so as not substantially affect delivery time once controller 80 receives a signal to initiate the delivery of medication 100). In other cases, the speed of advancement member 51 may be increased to ensure that pellet 100 completely exists the catheter and/or to even push it a minimum distance away from catheter tip 63 to prevent blockage of the tip and expedite disintegration of the medication pellet 100 at the delivery site DS.

Embodiments of apparatus 10 having an electro-mechanical or thermo-mechanical drive source 52 can also include a battery 55 or other electric power source for powering the drive source 52. Suitable batteries 55 include lithium, lithium-ion, lithium polymer, zinc-air, alkaline and other chemistries known in the electric battery art. Battery 55 may also be selected and configured to be rechargeable.

Referring back to FIG. 1, in various embodiments, belt drive mechanism 70 may correspond to a sprocket or other engageable advancement means 71 driven by a drive source 72 such as brushless DC motor, stepper motor, or other eletro-mechanical drive means 72. In some embodiments, drive means 72 may be one in the same as mechanism 52 with the addition of various gears or other motion control means (e.g., cams, linkages, etc.) for limiting the motion of sprocket 71 to one turn (and thus that of belt 40) for a complete advancement and withdrawal of advancement member 51 from and to housing 30. In other embodiments, drive source 72 and/or sprocket 71 is linked to drive mechanism 50 by a synchronizing mechanism or element 73, such as a belt, to achieve the desired level of synchronization between the motion of sprocket 71/belt 40 and advancement member 51 as is shown in FIG. 3A. In still other embodiments, the motion of sprocket 71/belt 40 and advancement member 51 can be synchronized electronically using controller 80, for example, using one or more software modules 83 (shown in FIG. 10) contained in a microprocessor based controller 80 as is described herein. Belt advancement mechanism or means 70 may also correspond to one or more of pinch rollers, magnetic, or electrical-based drive means known in the art.

Figure 7A:
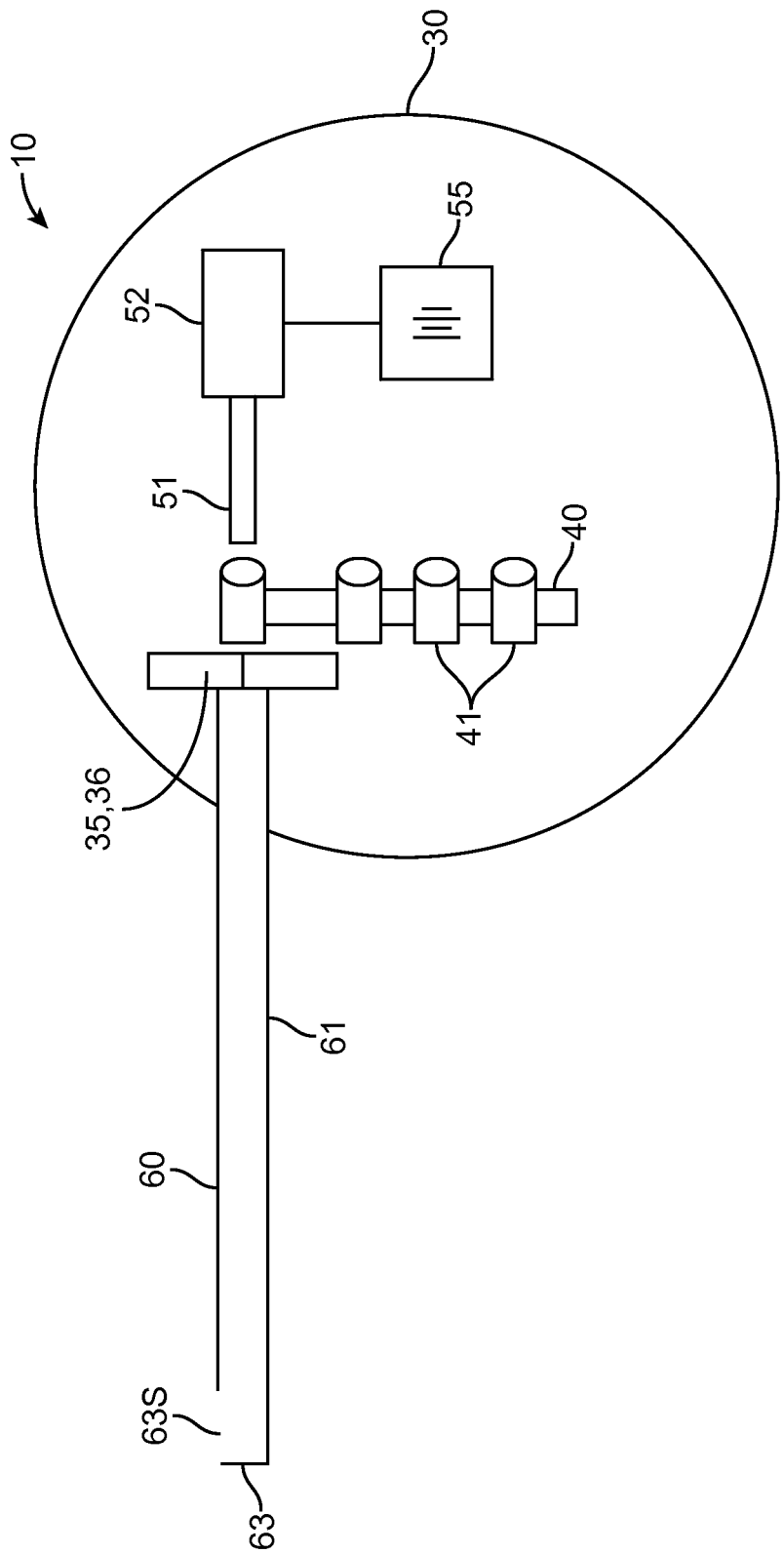
FIGS. 7A and 7B are side views showing operation of a shape memory metal drive source for use with a delivery mechanism.
Figure 7B:
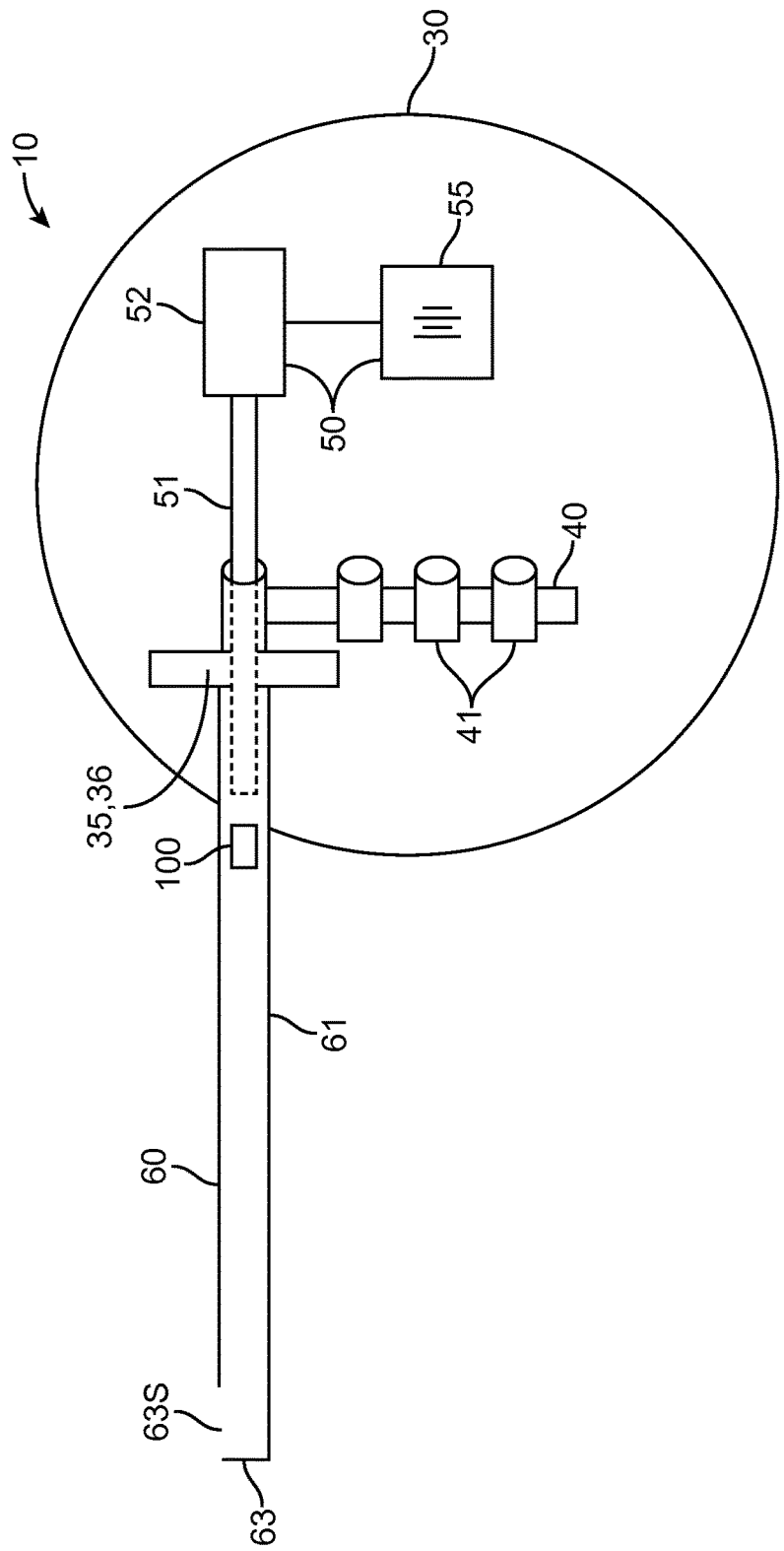

Referring now to FIGS. 7A-7B, in some embodiments, drive source 52 can comprise a nickel titanium wire (an example including NITINOL) or other shape memory material that changes length in response to heating, for example from an electrical current which can be supplied by battery 55 or other electric power source. In such embodiments, advancement member 51 itself may include portions of the thermally extendable shape memory wire.

Figure 8A:
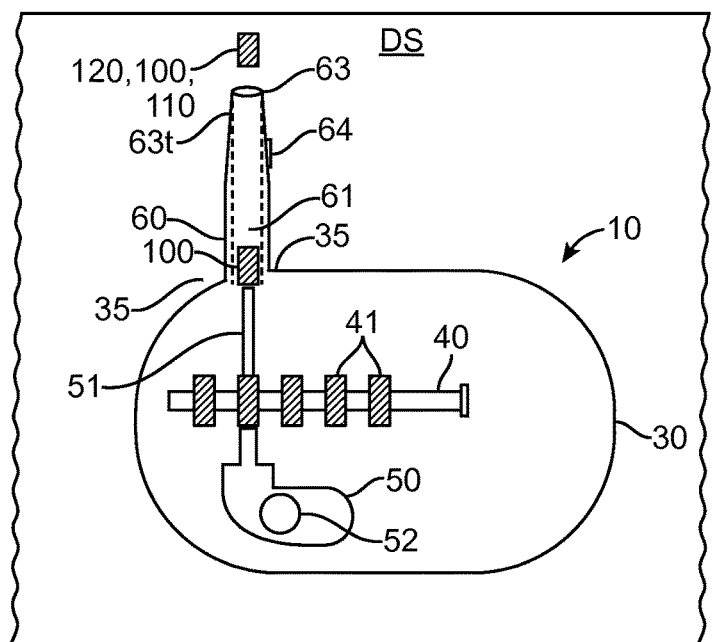
FIG. 8A is a side view illustrating an embodiment of a catheter used to deliver a medication pellet or other solid form of medication to a target tissue site in the body of a patient.

Referring now to FIG. 8A, in many embodiments, apparatus 10 includes an elongate member 60 attached to housing 30 for delivering a pellet 100 to a target tissue site. Elongate member 60 can comprise a catheter, metal hypo-tube, or other tubular structure known in the catheter and minimally invasive arts. For ease of discussion, member 60 will be referred to as delivery catheter 60 or catheter 60 but other forms described above are equally applicable. Catheter 60 can be fabricated from various polymeric materials known in the catheter arts including, polyethylene, PET, polyurethanes, silicones, PEBAX and the like. It may also be fabricated from various metallic materials including stainless steel, and various super-elastic metals shape memory materials such as nickel titanium alloys (an example including NITINOL). Catheter 60 has a lumen 61 sized to receive the medication pellet, a proximal end 62 positioned inside housing 30 (or coupled to opening 35) and an open distal end or tip 63 that extends outside of housing 30 to deliver the pellet to a delivery tissue site DS. In some embodiments, distal tip 63 may be blocked but include a slot 63*s* positioned on the side of the catheter 60 so as to allow advancement member 51 (or other advancement means) to push medication pellet 100 out the side of catheter 60. In various embodiments, the outer diameter 60D (see FIG. 1A) of catheter 60 can range from 0.5 to 4 mm and the length 60l (see FIG. 1A) from 1 to 10 cm with larger and smaller diameter and lengths contemplated. In particular embodiments, catheter 60 can have sufficient length to deliver pellet 100 to a different tissue site than the location of device 10 (for example, into the brain when the rest of apparatus 10 is located outside of the skull).

Also in particular embodiments, catheter 60 can be configured to provide all or a portion of the driving force for advancing pellet 100 from housing 30 to delivery site DS. The driving force can comprise a peristaltic like wave of contraction that travels distally along the length of the catheter. This can be achieved by constructing catheter 60 from either a piezoelectric or like material and coupling it to a voltage source or a shape memory material and coupling it to a thermal power source as is described herein. In the former case, the application of a voltage causes contraction of the catheter material and in the later case, the application of heat does so. In an alternative embodiment for transporting pellet 100 through catheter 60, pellet 100 can be charged or include a charged coating, such that the pellet is repelled from the catheter by the application of an electric voltage (having an opposite charge) to the catheter surface.

Desirably, distal catheter tip 63 has an atraumatic configuration to allow for extended periods of implantation at the target delivery site DS. This can be achieved by configuring the tip to have a tapered shape 63*t* as well as fabricating the tip from one or more atraumatic flexible polymeric materials including, for example, silicones polyurethanes, fluoropolymers, hydrogels, polyether block amides (PEBA) and others known in the art. Examples of specific atraumatic materials include silver-hydrogel and PEBAX (a PEBA). Catheter 60 including distal tip 63 can also include one or more sensors 64 for making various measurements at the delivery site DS. Such measurements can include drug concentration, pH, glucose, various metabolites, tissue $PO_2$ and $CO_2$ and the like.

Figure 8B:
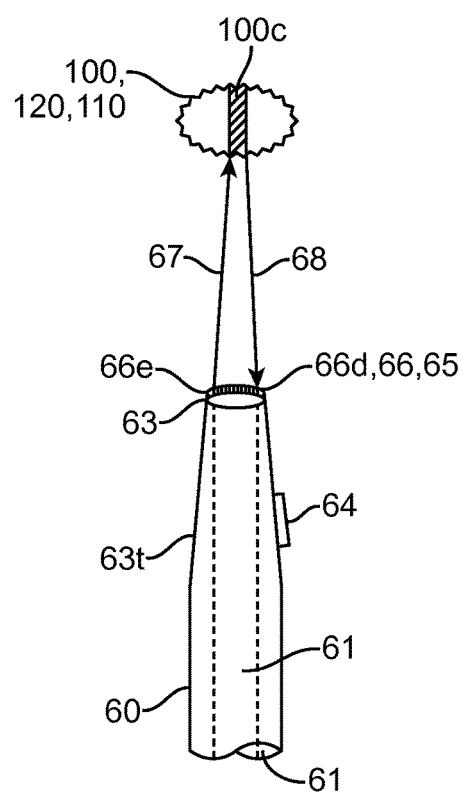
FIG. 8B is a side view illustrating use of an embodiment of a catheter having sensors for measuring the disintegration state of a medication pellet or other solid form of medication.
Figure 9A:
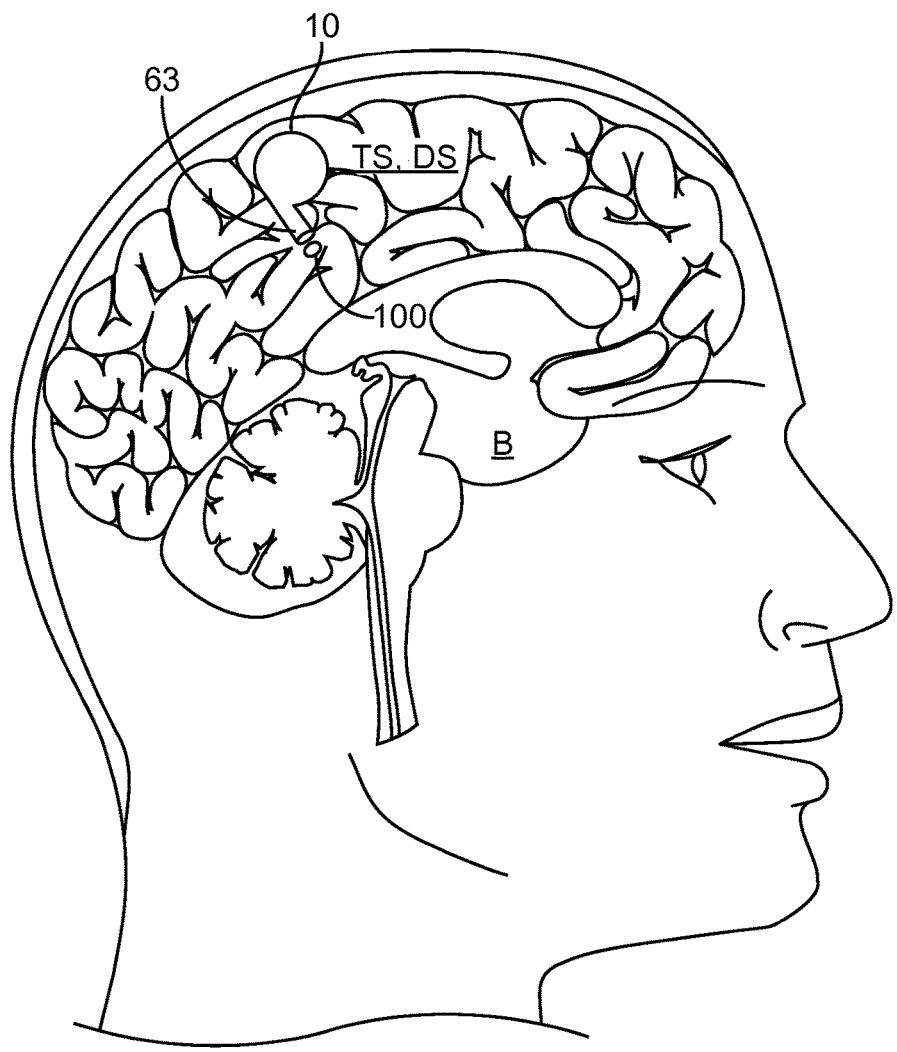
FIGS. 9A-9D show embodiments of the apparatus for placement at different locations in the body.
Figure 9B:
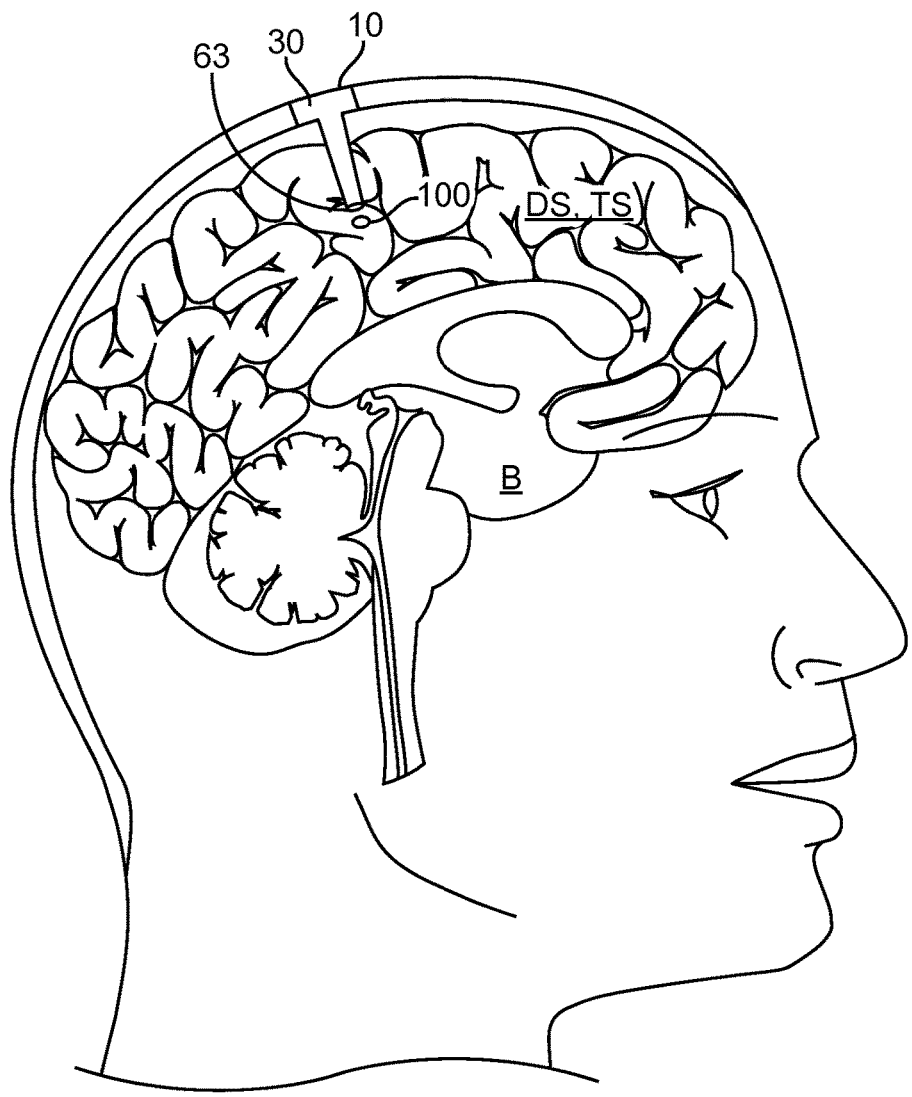
Figure 9C:
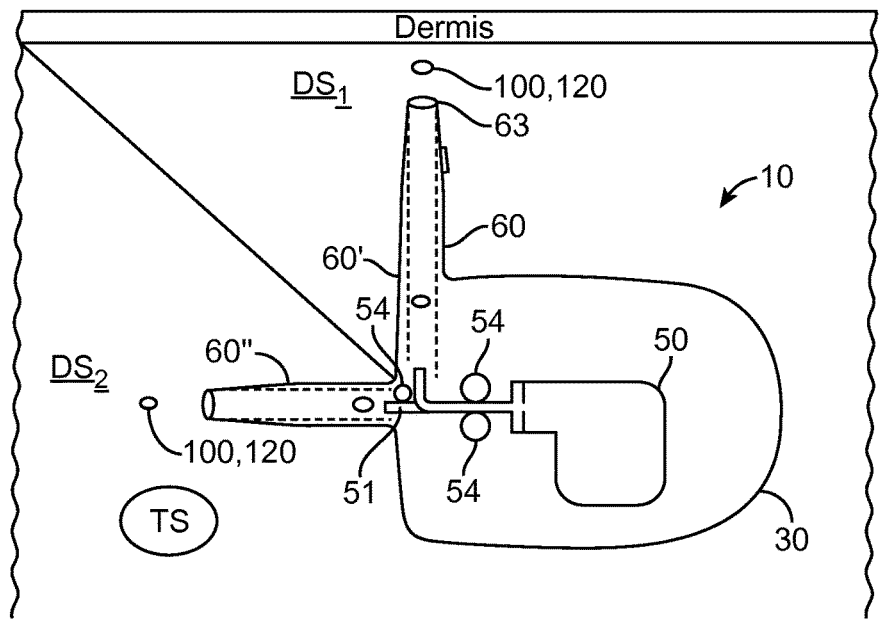
Figure 9D:
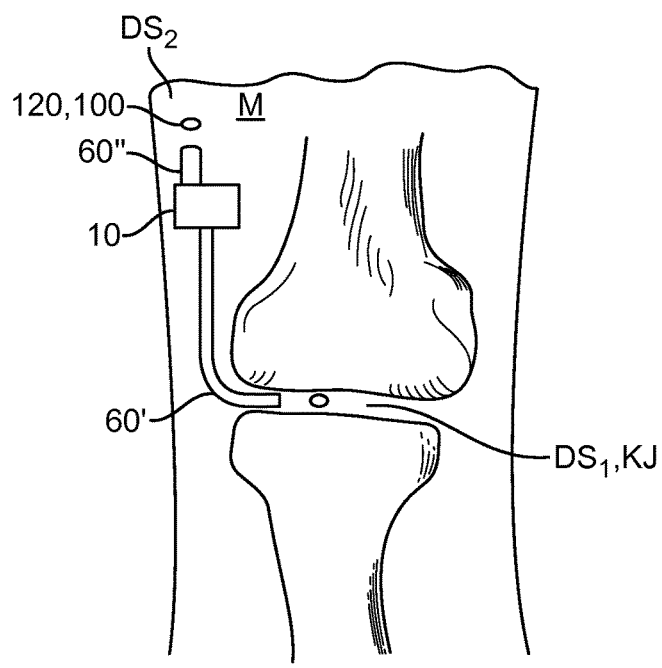

Referring now to FIG. 8B, in particular embodiments, sensor 64 can also comprise sensors 65 for making various measurements for determining the degradation/disintegration state of pellet 100. Suitable sensors 65 for making such measurements can comprise optical, impedance, acoustical and chemical sensors. Sensors 65 can also comprise an assembly 66 including an emitter 66e and detector 66d. Assembly 66 can include optical emitters and detectors for making reflectance measurements and ultrasonic transducers (configured as an emitter and detector) for making ultrasonic measurements. Assembly 66 sends or emits a signal 67 which is modulated or otherwise altered by the degradation/disintegration state of the pellet 100 and then reflected back by pellet 100 as a signal 68 which can then be analyzed to determine the degradation state of the pellet. For example, for use of an optical based assembly 66, signal 67 will be returned as a reflected signal 68 which progressively decreases in amplitude as the pellet is dissolved and disintegrated by body tissue fluids. As indicated above, in various embodiments, pellet 100 can include optical indicia 100c to facilitate measurement of the degradation state of pellet 100.

Embodiments of apparatus 10 having sensors 65 and/or sensor assembly 66 can be used to control or regulate pellet delivery by sensing the state of disintegration of previously delivered pellets. For example, another pellet can be delivered when it has been determined that the previous pellet is in a particular state of disintegration (e.g., it has been completely or substantially disintegrated). This determination can be achieved through use of a controller 80 described herein which may include one or more algorithms for analyzing the disintegration state of the pellet and using this information to make a delivery decision. In particular embodiments, information on the disintegration state of the pellet can be combined with other data for making a pellet delivery decision with weightings assignable to each group of data. Such additional data can include for example, the blood/plasma concentration of the delivered drug 110 as well as various physiological data (e.g., temperature, pH, blood gases, etc.) including physiological data indicative of the medical condition to be treated by the delivered drug 110, e.g., blood glucose as an indication of hyperglycemia, EKG as an indication of arrhythmia or brain electrical activity as an indication of an epileptic seizure or pre seizure event.

Referring now to FIGS. 9A-9D, in various embodiments, the length of the catheter 60 can be configured to allow the apparatus 10 to be positioned near the delivery site DS or to be positioned at a different location. For example, in one embodiment shown in FIG. 9A, apparatus 10 can be positioned in the brain B with the catheter tip 63 positioned a short distance away. In another embodiment shown in FIG. 9B, the catheter can have sufficient length to allow distal tip 63 to be positioned in the brain, while apparatus 10 is placed on the scalp or other location outside the skull. In this way, apparatus 10 can be used to deliver medication to a selectable delivery site DS, such as the brain without having to be placed at that site or have any appreciable effect on organs or tissue at that site other than that of the medication itself.

In some embodiments, apparatus 10 can include multiple catheters 60 so as to allow for the delivery of medication pellets 100 at multiple locations using a single delivery apparatus 10. For example, in an embodiment shown in FIG. 9C, the distal tip 63 of a first catheter 60' can be placed at first delivery site $DS_1$ and the distal tip 63 of a second catheter 60" can be placed a second delivery site $DS_2$. In an embodiment shown in FIG. 9D, the first delivery site $DS_1$ can comprise the ultimate target site TS such as an arthritic knee joint KJ (or other arthritic joint) to allow for immediate delivery of medication to that site and the second catheter distal tip can be placed at a second site $DS_2$ at least partially removed from first site $DS_1$ such as in muscle tissue M or other sub-dermal location to allow for longer term controlled release of a drug 110.

Figure 10:
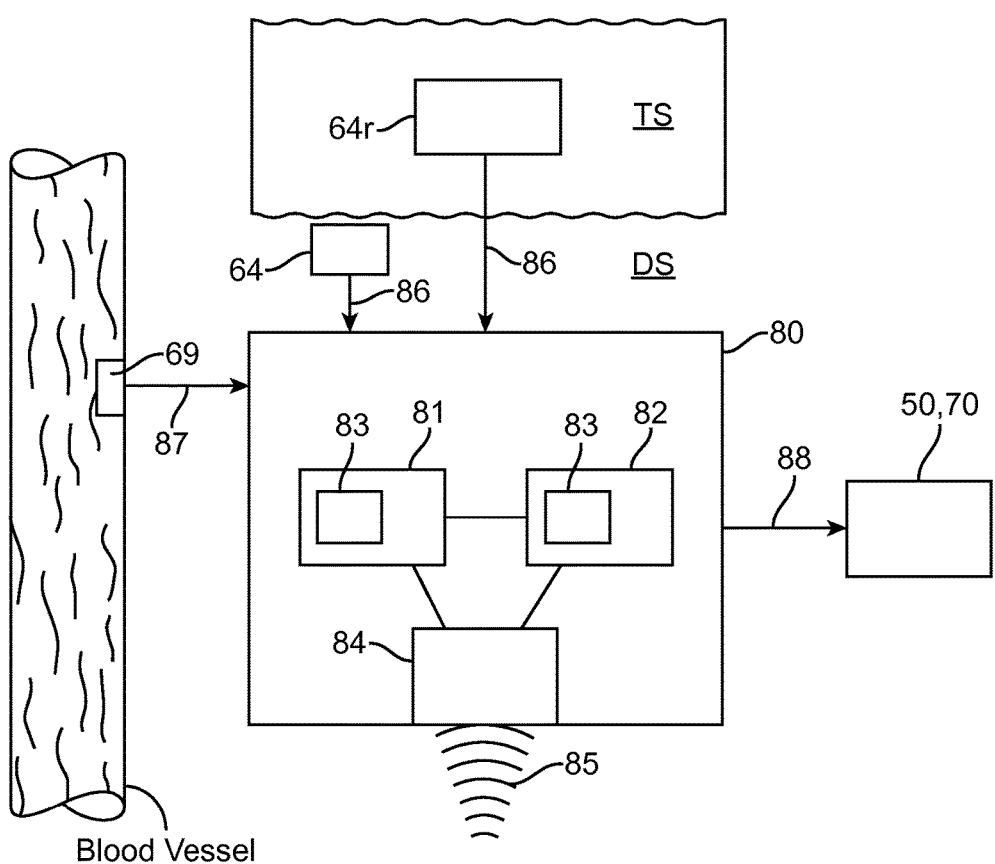
FIG. 10 is a schematic block diagram illustrating an embodiment of a controller for use with one or more embodiments of the solid drug delivery apparatus.

Referring now to FIG. 10, in many embodiments, apparatus 10 can include a controller 80 for controlling one or more aspects of the medication delivery process including actuation and control of mechanism 50 and/or 52. The controller can comprise logic resources 81 such as a microprocessor, a state device or both; and memory resources 82 such as RAM, DRAM, ROM, etc. Logic resources 81 and/or memory resources 82 may include one or more software modules 83 for operation of the controller 80. Through the use of modules 83, the controller 80 may be programmed to include a medication delivery regimen wherein medication is delivered at regular intervals (e.g., once or twice a day, etc.) over an extended period. The controller may also include an RF device 84 for receiving a wireless 85 signal (e.g., wireless or otherwise) to initiate the delivery of medication or to change the delivery regimen (e.g., from once a day to twice a day). In this way, the patient or a medical care provider can control the delivery of medication in response to a specific event (e.g., an episode of angina, an abnormal EKG) or longer term changes in the patient's condition or diagnosis.

The controller 80 can receive inputs 86 from apparatus sensor 64 or a remote sensor 64r which senses a physiologic parameter indicative of a condition to be treated by the medication pellet 100, e.g., diabetic hyperglycemia. When the controller 80 receives an input 86 indicative of the condition, it sends a signal 88 to initiate the delivery of one or more medication pellets 100 to the target tissue site so as to treat the medical condition. Both the initial and subsequent inputs from sensor 64 can be used to titrate the delivery of medication pellets over an extended period until the condition is dissipated or otherwise treated in a selected manner. The controller 80 can also receive inputs 87 from other sensors 69 which are configured to measure the plasma or other tissue concentration of the delivered drug 110. These inputs 87 can also be used to titrate the delivery of the drug to achieve a selected concentration of drug. The concentration sensors 69 can be positioned both at the delivery site DS, the target site TS as well as other sites in the body (e.g., a vein or artery) in order to develop a pharmacokinetic model of the distribution of the drug at multiple sites in the body.

Figure 11A:
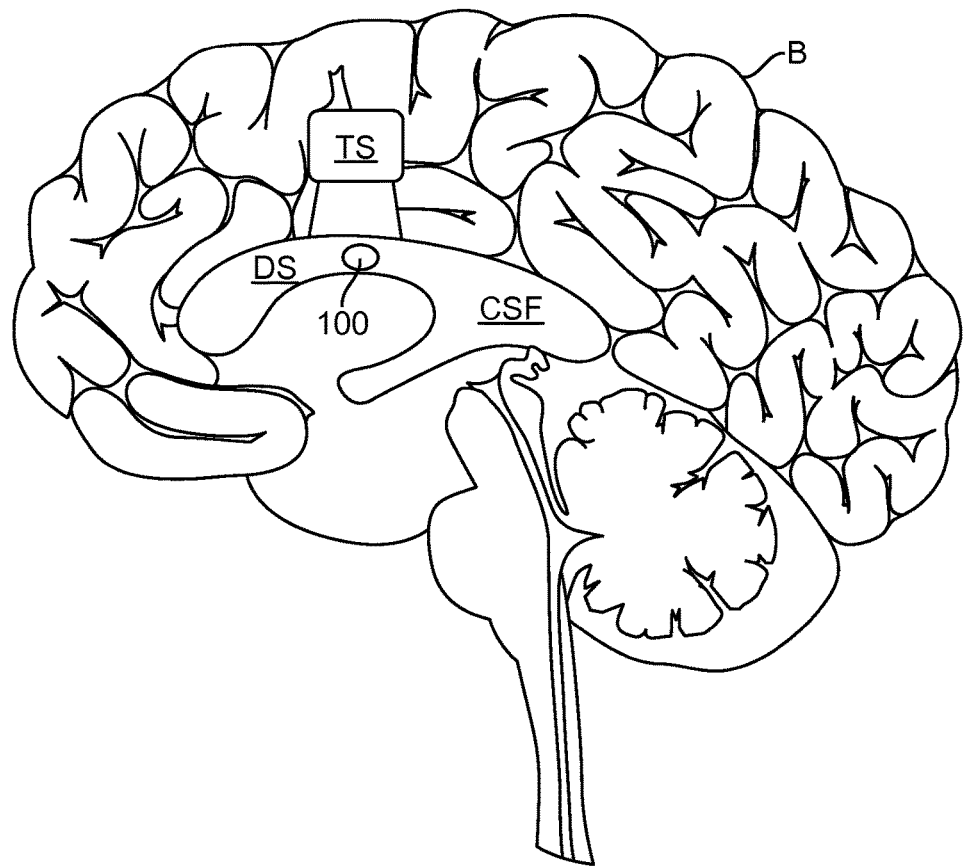
FIG. 11A shows placement of a medication pellet in a ventricle of the brain for dissolution and delivery of medication to a target site in the brain.
Figure 11B:
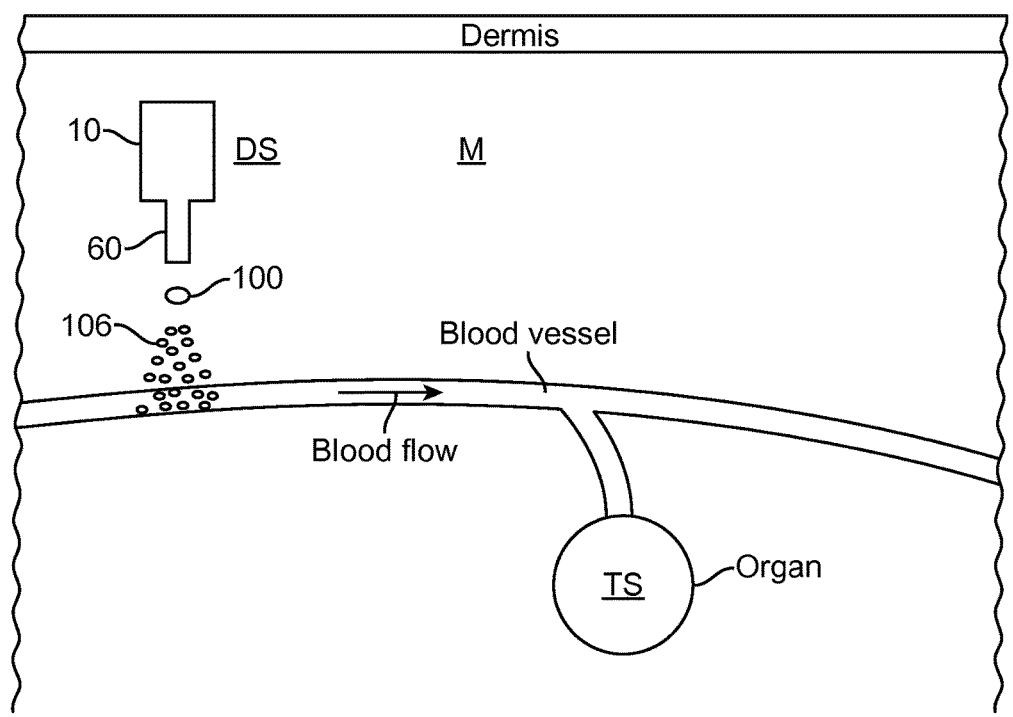
FIG. 11B shows placement of a medication/drug pellet at a delivery site for transport of the medication to a target tissue site removed from the delivery site.

In various method embodiments of the invention, apparatus 10 is used to deliver pellets or other solid form medication 100 to a selected delivery site DS such as subcutaneous tissue where they are disintegrated and absorbed by body tissue fluids (e.g., interstitial fluids in muscle or dermal tissue) so as to produce a desired concentration of drug 110 at a target site TS. Referring now to FIGS. 11A and 11B, in some embodiments for use of apparatus 10, the delivery site DS can be in the same organ and/or compartment as the target site TS, for example the brain as is shown in the embodiment of FIG. 11A. In other embodiments, the target site can be different from the delivery site as is shown in the embodiment of FIG. 11B. For example in one embodiment, the delivery site can be intramuscular tissue in the chest and the target site can be an organ such as the heart which is removed from the delivery site. The delivery site can be oppositional to the target site, for example dermal delivery to reach the target site of underlying muscle tissue, or it can be placed at a non-oppositional site, for example, intramuscular delivery to reach the target site of the heart. In each case, the medication pellet 100 can include a selected dose of drug and be configured to disintegrate and be dissolved by body tissue fluids so as to yield a therapeutically effective concentration of the drug at the target tissue site. In many applications, this involves the pellet being dissolved by body tissue fluids at the delivery site (e.g., interstitial fluids) where the drug then diffuses from the tissue into the blood stream where it is carried to the target tissue site. Accordingly, in these and other applications, the dose of the drug in the pellet can be titrated to achieve a selected plasma concentration of the drug (or concentration range) for a selected period during and after dissolution of the pellet.

In some embodiments, pellet 100 is configured to disintegrate and be dissolved by the tissue fluids within a body compartment such as the cerebrospinal fluid (CSF) in the brain so as to achieve a selected concentration in the tissue fluid within that compartment as is shown in the embodiment of FIG. 11A. In particular embodiments for treating various neural disorders such as epileptic and other seizures, pellet 100 is configured to rapidly disintegrate and be dissolved in cerebrospinal fluid (CSF) so as to rapidly achieve a selected concentration of the drug throughout the CSF that bathes the brain in order to prevent the occurrence of the seizure or lessen its duration and severity. This can be achieved through the use of one or more super-disintegrants which are compounded into pellet 100.

Figure 12A:
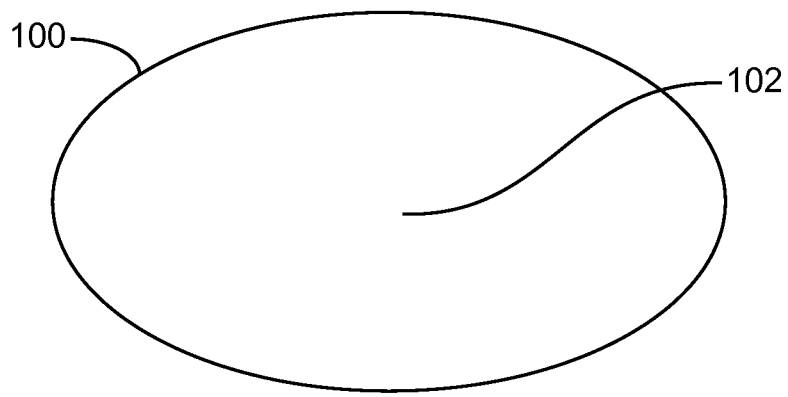
FIGS. 12A and 12B are side views of a medication pellet illustrating the delivery of force or energy to break down the pellet structure so as to enhance disintegration and dissolution of the pellet in the body.
Figure 12B:
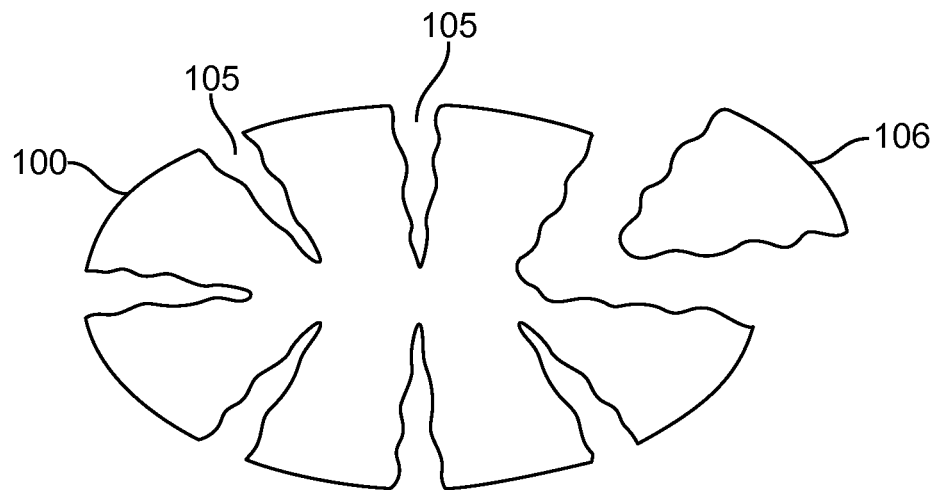
Figure 13:
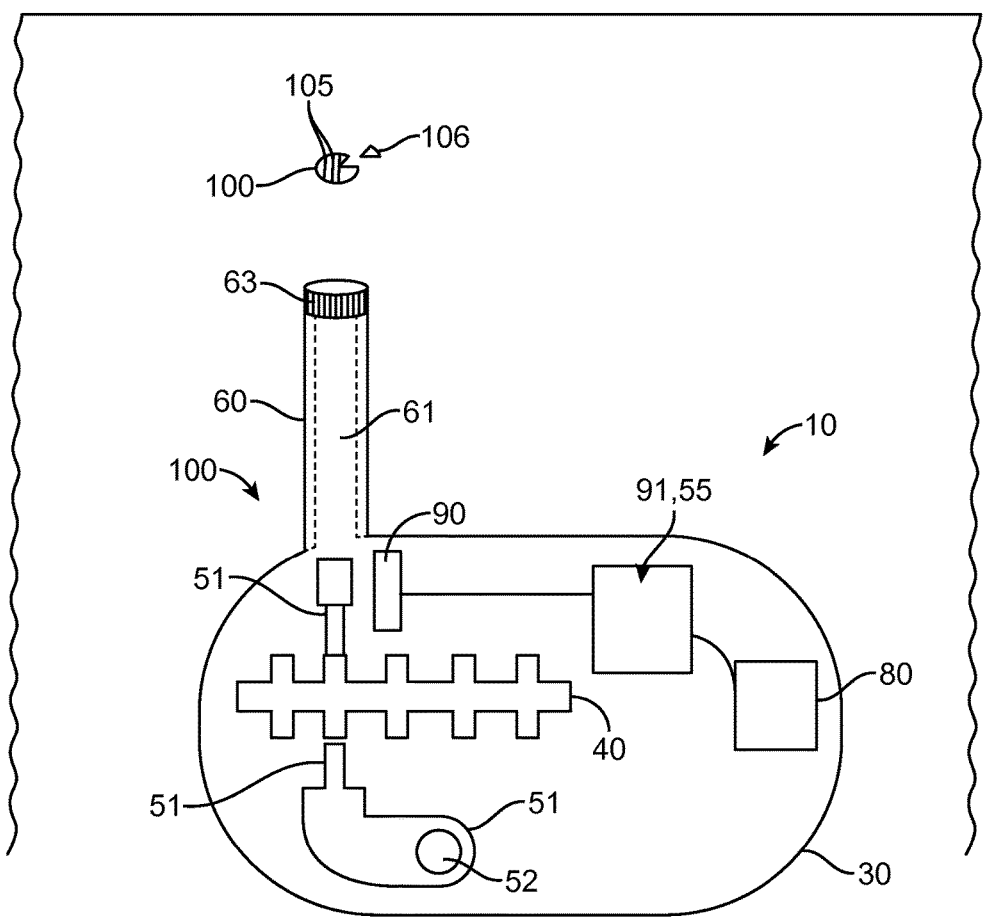
FIG. 13 is a side view illustrating the delivery of energy to the medication pellet prior to delivery to enhance dissolution of the pellet.
Figure 14:
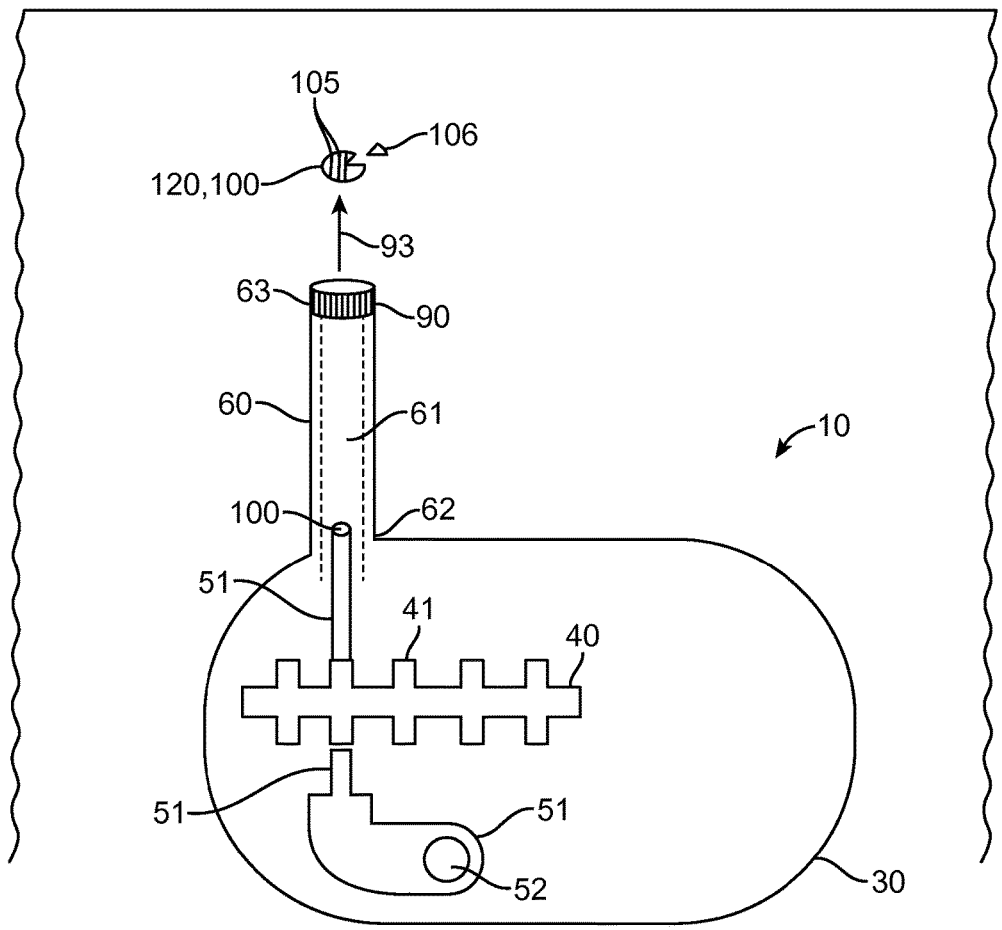
FIG. 14 is a side view illustrating the delivery of energy to the pellet after delivery to a delivery site to enhance to dissolution of the pellet.

Referring now to FIGS. 12-14, in other embodiments, accelerated disintegration of pellet 100 can also be achieved by treating the pellet prior to, during or after delivery with mechanical, electromagnetic, acoustical or other energy to weaken the pellet structure, create cracks for the ingress of fluids or initiate the breakup of the pellet into smaller pieces. As is shown in FIGS. 12A-12B, the delivery of force and energy can be used to create cracks 105 (or other surface defects) for the ingress of tissue fluids as well as break the pellet up into smaller pieces 106.

In other embodiments, energy can be delivered to the pellet 100 while it is still in the apparatus 10 to create cracks 105 and weaken the pellet structure as is shown in the embodiment of FIG. 13. In embodiments where advancement member 51 comprises medication 100 itself, energy can be delivered to create cracks or other structure weakness within discrete portions of the advancement member so as to cause discrete sections 51p of member 51 to break off (e.g., typically the distal most section) corresponding to a dose 100d of medication 100 to deliver medication 100 to delivery site DS. In one more embodiments, energy delivery can be achieved through use of an acoustical energy device 90 such as an ultrasonic transducer with the ultrasonic frequency configured for a resonant frequency of pellet 100. Acoustical or other energy device 90 can be coupled to an energy source 91, which can include various electrical power sources, and may be the same as battery 55 used to power drive source 72 and/or delivery mechanism 50).

In another embodiment shown in FIG. 14, energy can be delivered to the pellet after it is ejected from catheter 60 and delivered to delivery site DS. In this embodiment, energy delivery can be achieved through use of an ultrasonic transducer or other energy delivery device 90 placed on catheter distal tip 63. Ultrasonic transducer 90 emits a beam of energy 93 which acts upon pellet 100 to cause cracks 105 and other effects to the pellet structure to accelerate pellet degradation into pieces 106 and disintegration through dissolution by body tissue fluids. Other forms of energy which can be used to break up and/or weaken the structure of pellet 100 and accelerate disintegration/degradation include optical (e.g., laser), RF, microwave, thermal or other forms of energy known in the medical device arts. The energy delivery regimen (e.g., duration, frequency and amount of energy) for weakening the pellet structure (e.g., causing cracks etc.) can be controlled by controller 80. The energy delivery regimen can be adjusted depending upon the size and structure properties of the pellet as well as the particular delivery site DS. In various embodiments, energy delivery device 90 can be powered by power source 55 or have its own power source.

Figure 15A:
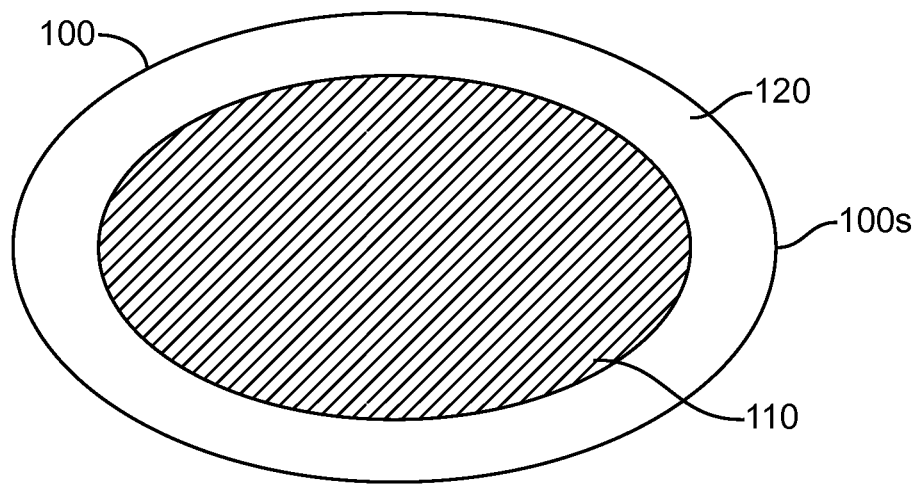
FIG. 15A is a side view illustrating an embodiment of the medication pellet.

Referring now to FIG. 15A, as indicated previously solid form medication also described herein as medication 100 or formulation 100 will typically be formulated into pellets 100, though other solid formulations are also contemplated, such as powder, granules and the like. For ease of discussion, solid form medication 100 will now be referred to as medication pellets 100 and/or pellets 100, but it will be appreciated that other forms of solid medication 100 are equally applicable. Also as used herein, the term medication comprises a drug 110 or other therapeutic agent 110 and one or more pharmaceutical excipients 120. Other therapeutic agents 110 can include for example, antibodies, vaccines, micro-nutrients and like agents. Accordingly, each pellet 100 contains a selected dose of a drug or other therapeutic agent 110 to treat a particular medical condition such as Furosemide for the treatment of epilepsy. The dose can be selected based on the patient's weight and age. Also in many embodiments, the medication pellets 100 can be formulated using one or more pharmaceutical excipients 120. Suitable excipients 120 include preservatives for preserving the drug, binders for binding the drug components together and disintegrants for disintegrating and dissolving the pellets in a controlled fashion to achieve and maintain a sufficient concentration of the drug (either at the tissue site or other tissue location) for treatment of the condition. As is described herein, disintegrants 120 can include super-disintegrants known in the art. Example super-disintegrants include sodium starch glycolate, crospovidone, croscarmellose sodium as well as related salts and like compounds.

Pellets 100 can have a selectable size and shape 100s and can comprise any number of drugs or other therapeutic agents and can be fabricated using various pharmaceutical manufacturing methods including lyophilization. In particular embodiments, pellets 100 can have round, oval or other shape. In one or more preferred embodiments, pellet 100 has a cylindrical shape so that it can be packaged within individual compartments 42 of belt 40. The size and shape of pellet 100 can be selected based upon one or more of the required dose of the drug, the desired disintegration rate and the delivery site. The shape can also be selected for optimized packing into belt 40 or other like element. Particular embodiments of pellets 100 can be shaped and sized to allow for packing of 50, 100, 200 or more pellets onto belt, 40. The pellets 100 are also desirably fabricated so as to have a product life of years when stored in vivo, for example two to five years or longer so that the drug maintain its potency and therapeutic effectiveness. Such product lives can be achieved through the use of sealed drug compartments 41 as well as the use of preservatives and lyophilization of one or more of the chemical components comprising pellet 100 such that pellets 100 including drugs 110 neither substantially degrade nor suffer other deleterious effects (e.g., effects which reduce the potency or therapeutic efficacy of the drug, for example, wherein the potency or therapeutic efficacy of the drug is reduced by no more than 10, or 1, or 0.1%) while stored in compartments 41. Referring back to FIG. 1, shelf lives of pellets 100 can also be increased by constructing housing 30 to have a substantially hermetic seal for example through use of impermeable layers 34, to minimize degradation or other deleterious effect occurs to pellet 100 from exposure to moisture, air or other ambient condition which may cause degradation of pellet 100. Also, the interior 31 of housing 30 can include a desiccant such as a Zeolite desiccant to absorb any water vapor that may get into housing 30. Use of the seal for housing 30 alone and/or with a desiccant allows housing interior 31 to remain substantially isolated from the environment of the body and thus extend the shelf life of pellets 100.

In various embodiments, pellets 100 can comprise a single or a plurality of drugs 110. In particular embodiments, pellets 100 can include a combination of drugs for treatment of a single or multiple conditions, for example, a cocktail of antiviral drugs such as protease inhibitors for treatment of HIV AIDS and also antibiotics for the treatment of adjunct bacterial infections.

Figure 15B:
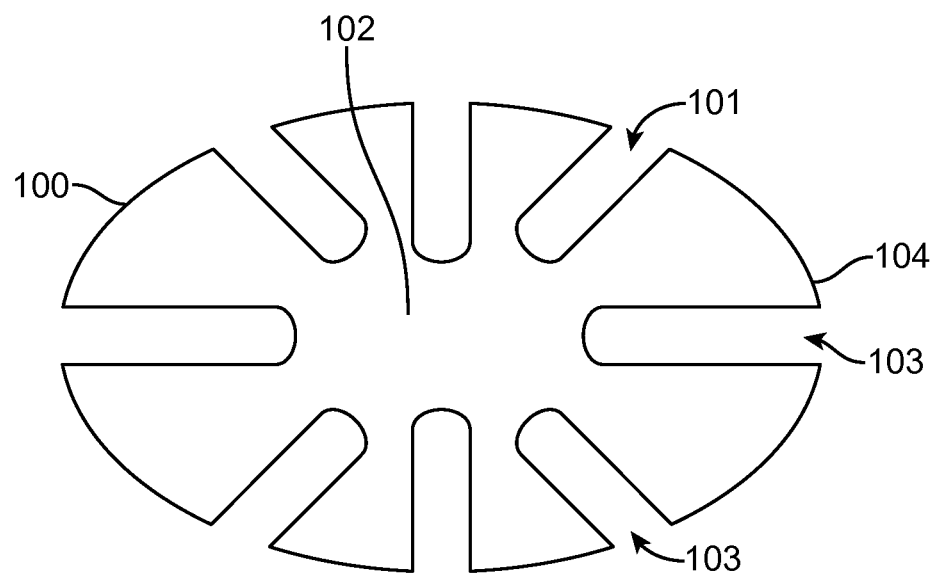
FIG. 15B is a side view illustrating an embodiment of the medication pellet having features for accelerating degradation and dissolution of the pellet by body tissue fluids.
Figure 15C:
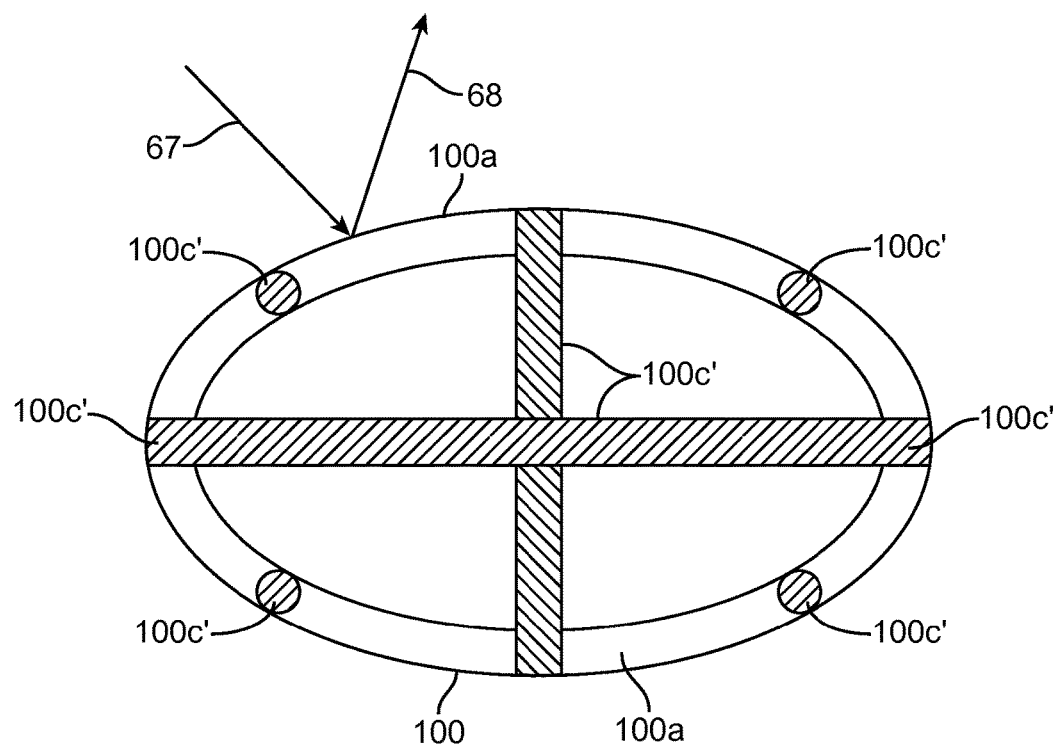
FIG. 15C is a side view illustrating an embodiment of the medication pellet having coatings and optical indicia for measurement of pellet degradation/disintegration by body tissue fluids.

Referring now to FIGS. 15B and 15C, in various embodiments, pellets 100 can include various features and chemical agents to enhance the degradation/disintegration of the pellet as well as quantify the amount and rate of disintegration (as used herein with respect to pellet 100 the terms degrade and disintegrate are essentially interchangeable. In various embodiments, the pellet can be porous or and/or include one or more channels 101 extending inwards from the pellet surface to facilitate the ingress (through capillary action) of body tissue fluids within pellet interior 102 to accelerate disintegration of the pellet by dissolution. In particular embodiments, channels 101 can be arranged in a pattern 103 so as to result in a substantially uniform ingress of body tissue fluids along the pellet circumference 104 as is show in the embodiment of FIG. 15B.

Referring now to FIG. 15C, in various embodiments, pellets 100 can include echogenic, or optically reflective agents 100a to enhance the reflected an acoustical or optical signal reflected off of pellet 100. As is discussed herein, such signals can be used to quantify the amount of disintegration of pellet 100. The pellet 100 may also include various optical indicia 100c having one or more of a pattern, size or shape configured to provide an indication of the state of disintegration of the pellet. The patterns can be configured to enhance reflectance (optical or acoustic), or contrarily to enhance scattering. Multiple indicia having different patterns (e.g., some reflective some causing scattering) can be positioned at several locations on the pellet. The size and shape of the indicia 100c can be used to determine a total amount of disintegration as well as a rate of disintegration, e.g., the smaller the size of the indicia the more disintegration has occurred with the rate of size decrease of the indicia being correlative to a rate of disintegration. Various calibration measurements may be made (e.g., measuring pellet mass and indicia size over the time course of disintegration) to establish the precise correlative relationship between rate of indicia loss and pellet disintegration (e.g., first order, second order, etc.). In particular embodiments, indicia 100c can comprise lines, rectangles, or ovals extending over all or a portion of the length and width of pellet 100 as is shown in the embodiment of FIG. 15C. Other contemplated shapes for indicia 100i include circles and various intersecting shapes such as a crisscross shape. Indicia 100c may also be placed at various locations along the perimeter 104 of pellet 100.

In various applications, embodiments of the invention can be used to deliver pellets 100 or solid form medication to provide treatment for a number of medical conditions including epileptic seizures (e.g., by use of Furosemide), high blood pressure (e.g., by use of calcium channel blockers, CCBs), elevated cholesterol (e.g., by use of LIPITOR), diabetes (e.g., by use of insulin), coronary arrhythmia's (both atrial and ventricular, e.g., by use of CCB's), coronary ischemia (e.g., by use of nitroglycerin or other vasodilating agent), or cerebral ischemia, heart attack or stroke (e.g., by use of aspirin, TPA or other hemolytic agent), anemia (e.g., by use of ferric-pyrophosphate) or other like conditions. Further embodiments of the invention can be used to provide concurrent treatment for two or more of these or other conditions eliminating the need for the patient to take multiple doses of different drugs (e.g., orally or by parenteral means) over the course of a day. This is particularly beneficial to patients who have long term chronic conditions including those who have impaired cognitive or physical abilities.

CONCLUSION

The foregoing description of various embodiments of the invention has been presented for purposes of illustration and description. It is not intended to limit the invention to the precise forms disclosed. Many modifications, variations and refinements will be apparent to practitioners skilled in the art. For example, embodiments of the apparatus can be sized and otherwise adapted for various pediatric and neonatal applications as well as various veterinary applications (e.g., for a dog, cat, horse, cow and other mammals).

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as stand-alone elements. Hence, the scope of the present invention is not limited to the specifics of the described embodiments, but is instead limited solely by the appended claims.

What is claimed is:

1. A method for delivering solid form medication within a body of a patient, the method comprising:
   implanting a container in the body, wherein said container carries a plurality of doses of a solid form medication, each dose being in an individual sealed packaging configured to preserve said doses for an extended period without substantial degradation or deleterious effect to the medication, wherein the medication comprises a drug for the treatment of a disease or condition; and
   advancing an advancement member within the container to puncture opposite ends of a single individual sealed packaging to remove the dose of solid form medication from the sealed packaging; and
   continuing to advance the advancement member to deliver the dose of solid form medication from the container after it has been removed from the sealed packaging to a delivery site outside of the container and within the body of the patient so as to produce a therapeutic effect at a target tissue site for the treatment of the disease or condition.

2. The method of claim 1, wherein each sealed packaging comprises a hermetically sealed packaging.

3. The method of claim 1, wherein the plurality of doses of medication are carried by a belt.

4. The method of claim 3, wherein the belt is advanced with a delivery of each dose of medication to align a next individual sealed packaging with the advancement member.

5. The method of claim 1, wherein the deleterious effect comprises a loss of potency or therapeutic effectiveness of the drug.

6. The method of claim 1, further comprising: dissolving the delivered solid form dose of medication at the delivery site to yield a therapeutically effective amount of the drug at the target tissue site.

7. The method of claim 1, wherein the medication comprises a pharmaceutical excipient.

8. The method of claim 1, wherein the extended period is up to about five years.

9. The method of claim 1, wherein the solid form medication is delivered at regular intervals.

10. The method of claim 9, wherein the interval is about an hour, 8 hours, 12 hours, 1 day, 2 days or 7 days.

11. The method of claim 1, wherein the solid form medication is delivered in response to a sensed physiological parameter.

12. The method of claim 11, wherein the sensed physiological parameter is predictive of a medical condition, a neurological seizure, an epileptic seizure, an arrhythmia, hypertension or hyperglycemia.

13. The method of claim 1, wherein the dose of medication comprises a drug for the treatment of epilepsy.

14. The method of claim 1, wherein the dose of medication comprises a drug for the treatment of an arrhythmia.

15. The method of claim 1, wherein the dose of medication comprises a drug for the treatment of diabetes.

16. The method of claim 1, wherein the dose of medication comprises a drug for the treatment of angina.

17. The method of claim 1, further comprising implanting the container within the body of the patient.

18. A method for delivering a solid form dose of medication for the treatment epilepsy, the method comprising:
    implanting a container adjacent a skull of a patient, wherein said container carries a plurality of doses of solid form medication in an individual sealed packaging configured to preserve said doses for an extended period without substantial degradation or deleterious effect to the medication, wherein the medication comprises a drug for the treatment of an epileptic seizure;
    advancing an advancement member within the container to puncture opposite ends of a single individual sealed packaging to remove the dose of solid form medication from the sealed packaging; and
    continuing to advance the advancement member to deliver the dose of solid form medication from the container after it has been removed from the sealed packaging to a delivery site within brain tissue so as to prevent an epileptic seizure or decrease the severity or duration of an epileptic seizure.

19. The method of claim 18, wherein the drug comprises furosemide.

20. The method of claim 18, further comprising: rapidly dissolving the delivered solid form medication within the cerebrospinal fluid (CSF) of the brain to achieve a selected concentration of the drug within the CSF to prevent the epileptic seizure or lessen the severity or duration of the epileptic seizure.

* * * * *